(12) United States Patent
Baker, Jr.

(10) Patent No.: US 10,201,302 B2
(45) Date of Patent: *Feb. 12, 2019

(54) SYSTEMS AND METHODS FOR DETERMINING WHETHER REGIONAL OXIMETRY SENSORS ARE PROPERLY POSITIONED

(71) Applicant: Covidien LP, Mansfield, MA (US)

(72) Inventor: Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/867,208

(22) Filed: Jan. 10, 2018

(65) Prior Publication Data

US 2018/0146897 A1    May 31, 2018

Related U.S. Application Data

(63) Continuation of application No. 14/605,891, filed on Jan. 26, 2015, now Pat. No. 9,867,561.

(60) Provisional application No. 61/932,045, filed on Jan. 27, 2014.

(51) Int. Cl.
*A61B 5/1455* (2006.01)
*A61B 5/1495* (2006.01)
*A61B 5/00* (2006.01)

(52) U.S. Cl.
CPC ........ *A61B 5/1495* (2013.01); *A61B 5/14551* (2013.01); *A61B 5/684* (2013.01); *A61B 5/7221* (2013.01)

(58) Field of Classification Search
CPC .............. A61B 5/1455; A61B 5/14551; A61B 5/14552; A61B 5/1495; A61B 5/684; A61B 5/72; A61B 5/7221
See application file for complete search history.

(56) References Cited

U.S. PATENT DOCUMENTS

| 5,115,133 | A | 5/1992 | Knudson |
| 5,187,672 | A | 2/1993 | Chance et al. |
| 5,222,495 | A | 6/1993 | Clarke et al. |

(Continued)

OTHER PUBLICATIONS

Allen, "Photoplethysmography and its Application in Clinical Physiological Measurements," Physiol. Meas., vol. 28, pp. R1-R39, Mar. 2007.

(Continued)

*Primary Examiner* — Eric Winakur
(74) *Attorney, Agent, or Firm* — Shumaker & Sieffert, P.A.

(57) ABSTRACT

Methods and systems are presented for determining whether a regional oximetry sensor is properly positioned on a subject. First and second metric values may be determined based on respective first and second light signals. The first and second metric values and a relationship between the first and second metrics are used to determine whether the sensor is properly positioned on the subject. The first and second metrics may form a pair of metrics, and whether the sensor is properly positioned on the subject may be determined based on whether the pair of metrics falls within a sensor-on region. In some embodiments, a plurality of metrics may be determined based on a plurality of received physiological signals. The plurality of metrics may be combined, using, for example, a neural network, to determine whether the regional oximetry sensor is properly positioned on a subject.

24 Claims, 10 Drawing Sheets

(56) References Cited

U.S. PATENT DOCUMENTS

| | | | |
|---|---|---|---|
| 5,277,181 A | 1/1994 | Mendelson et al. |
| 5,299,570 A | 4/1994 | Hatschek |
| 5,419,321 A | 5/1995 | Evans |
| 5,440,388 A | 8/1995 | Erickson |
| 5,482,034 A | 1/1996 | Lewis et al. |
| 5,503,148 A | 4/1996 | Pologe et al. |
| 5,661,302 A | 8/1997 | Evans et al. |
| 5,673,701 A | 10/1997 | Chance |
| 5,747,806 A | 5/1998 | Khalil et al. |
| 5,770,454 A | 6/1998 | Essenpreis et al. |
| 5,803,910 A | 9/1998 | Potratz |
| 5,820,558 A | 10/1998 | Chance |
| 5,825,488 A | 10/1998 | Kohl et al. |
| 5,830,132 A | 11/1998 | Robinson |
| 5,902,235 A | 5/1999 | Lewis et al. |
| 5,954,053 A | 9/1999 | Chance et al. |
| 5,983,122 A | 11/1999 | Jarman et al. |
| 6,035,223 A | 3/2000 | Baker, Jr. |
| 6,058,324 A | 5/2000 | Chance |
| 6,122,535 A | 9/2000 | Kaestle et al. |
| 6,236,047 B1 | 5/2001 | Malin et al. |
| 6,278,889 B1 | 8/2001 | Robinson |
| 6,353,226 B1 | 3/2002 | Khalil et al. |
| 6,360,114 B1 | 3/2002 | Diab et al. |
| 6,385,471 B1 | 5/2002 | Mortz |
| 6,438,399 B1 | 8/2002 | Kurth |
| 6,510,329 B2 | 1/2003 | Heckel |
| 6,549,795 B1 | 4/2003 | Chance |
| 6,615,061 B1 | 9/2003 | Khalil et al. |
| 6,615,065 B1 | 9/2003 | Barrett et al. |
| 6,708,048 B1 | 3/2004 | Chance |
| 6,771,994 B2 | 8/2004 | Kiani et al. |
| 6,819,950 B2 | 11/2004 | Mills |
| 7,098,037 B2 | 8/2006 | Haas et al. |
| 7,130,671 B2 | 10/2006 | Baker, Jr. et al. |
| 7,187,960 B2 | 3/2007 | Abreu |
| 7,271,912 B2 | 9/2007 | Sterling et al. |
| 7,315,752 B2 | 1/2008 | Kraemer et al. |
| 7,356,365 B2 | 4/2008 | Schurman |
| 7,424,317 B2 | 9/2008 | Parker et al. |
| 8,265,723 B1 | 9/2012 | McHale et al. |
| 8,352,004 B2 | 1/2013 | Mannheimer et al. |
| 8,436,348 B2 | 1/2013 | Onimura |
| 8,696,585 B2 | 4/2014 | Addison et al. |
| 8,821,397 B2 | 9/2014 | Al-Ali et al. |
| 8,965,472 B2 | 2/2015 | Benni |
| 9,326,712 B1 | 5/2016 | Kiani |
| 9,867,561 B2 | 1/2018 | Baker, Jr. |
| 2008/0228053 A1 | 9/2008 | Wang et al. |
| 2011/0208024 A1 | 8/2011 | Widman et al. |
| 2014/0175261 A1 | 6/2014 | Addison et al. |
| 2014/0176944 A1 | 6/2014 | Addison et al. |
| 2014/0243633 A1 | 8/2014 | Addison et al. |
| 2014/0275882 A1 | 9/2014 | Addison et al. |
| 2014/0371548 A1 | 12/2014 | Al-Ali et al. |
| 2015/0099950 A1 | 4/2015 | Al-Ali et al. |

OTHER PUBLICATIONS

Murray, et al., "The Peripheral Pulse Wave: Information Overlooked," J. Clin. Monit., vol. 12, No. 5, pp. 365-377, Sep. 1996.

Shelley, "Photoplethysmography: Beyond the Calculation of Arterial Oxygen Saturation and Heart Rate," Anesth. Analg. vol. 105, No. 6, pp. S31-S36, Dec. 2007.

Notice of Allowance from U.S. Appl. No. 14/605,891, dated Sep. 14, 2017, 9 pages.

Chuan et al., "Is cerebrovascular autoregulation associated with outcomes after major noncardiac surgery? A prospective observational pilot study," Acta Anaesthesiol Scand., Aug. 5, 2018, 10 pages.

500

```
┌─────────────────────────────────────────┐
│   Receive first and second light signals │
│                  502                     │
└─────────────────────────────────────────┘
                    │
                    ▼
┌─────────────────────────────────────────┐
│ Determine first and second metric values based on the │
│    received first and second light signals │
│                  504                     │
└─────────────────────────────────────────┘
                    │
                    ▼
┌─────────────────────────────────────────┐
│ Determine, based on the first and second metric values and a │
│ relationship between the first and second metrics, whether the │
│ regional oximetry sensor is properly positioned on the subject. │
│                  506                     │
└─────────────────────────────────────────┘
```

```
┌─────────────────────────────────────────┐
│  Receive a plurality of physiological signals  │
│                    902                          │
└─────────────────────────────────────────┘
                    ↓
┌─────────────────────────────────────────┐
│         Receive sensor information              │
│                    904                          │
└─────────────────────────────────────────┘
                    ↓
┌─────────────────────────────────────────┐
│ Determine a plurality of metrics based on the plurality of │
│              physiological signals              │
│                    906                          │
└─────────────────────────────────────────┘
                    ↓
┌─────────────────────────────────────────┐
│ Determine, based on the plurality of metrics and/or the │
│ sensor information, whether the sensor is properly positioned │
│                on a subject                     │
│                    908                          │
└─────────────────────────────────────────┘
                    ↓
┌─────────────────────────────────────────┐
│ Determine regional oxygen saturation when it is determined │
│   that the sensor is properly positioned on the subject │
│                    910                          │
└─────────────────────────────────────────┘
```

FIG. 9

SYSTEMS AND METHODS FOR DETERMINING WHETHER REGIONAL OXIMETRY SENSORS ARE PROPERLY POSITIONED

CROSS REFERENCE TO RELATED APPLICATION

This application is a continuation of U.S. patent application Ser. No. 14/605,891, filed Jan. 26, 2015, now allowed, which claims the benefit of U.S. Provisional Application No. 61/932,045, filed Jan. 27, 2014, each of which are hereby incorporated by reference herein in their entirety.

SUMMARY

The present disclosure relates to determining whether a sensor is properly positioned on a subject, and more particularly, relates to determining whether a regional oximetry sensor is properly positioned on a subject.

Methods and systems are provided for determining whether regional oximetry sensors are properly positioned on tissue of a subject.

In some embodiments, a system for determining whether a regional oximetry sensor is properly positioned on a subject includes one or more inputs configured for receiving a first signal representative of an intensity of light at a first detector of the regional oximetry sensor, and receiving a second signal representative of an intensity of light at a second detector of the regional oximetry sensor. The system further includes one or more processors configured for determining a first metric value based on the first signal, and determining a second metric value based on the second signal. The one or more processors are further configured for determining, based on the first metric value, the second metric value, and a relationship between the first metric and the second metric, whether the regional oximetry sensor is properly positioned on the subject.

In some embodiments, a method for determining whether a regional oximetry sensor is properly positioned on a subject comprises receiving a first signal representative of an intensity of light at a first detector of the regional oximetry sensor, and receiving a second signal representative of an intensity of light at a second detector of the regional oximetry sensor. The method also includes determining a first metric value based on the first signal, and determining a second metric value based on the second signal. The method also includes determining, based on the first metric value, the second metric value, and a relationship between the first metric and the second metric, whether the regional oximetry sensor is properly positioned on the subject.

BRIEF DESCRIPTION OF THE FIGURES

The above and other features of the present disclosure, its nature and various advantages will be more apparent upon consideration of the following detailed description, taken in conjunction with the accompanying drawings in which:

FIG. 5 shows an illustrative flow diagram including steps for determining whether a sensor is properly positioned on a subject in accordance with some embodiments of the present disclosure;

FIG. 9 shows an illustrative flow diagram including steps for determining whether a sensor is properly positioned on a subject in accordance with some embodiments of the present disclosure.

DETAILED DESCRIPTION OF THE FIGURES

Figure 1:
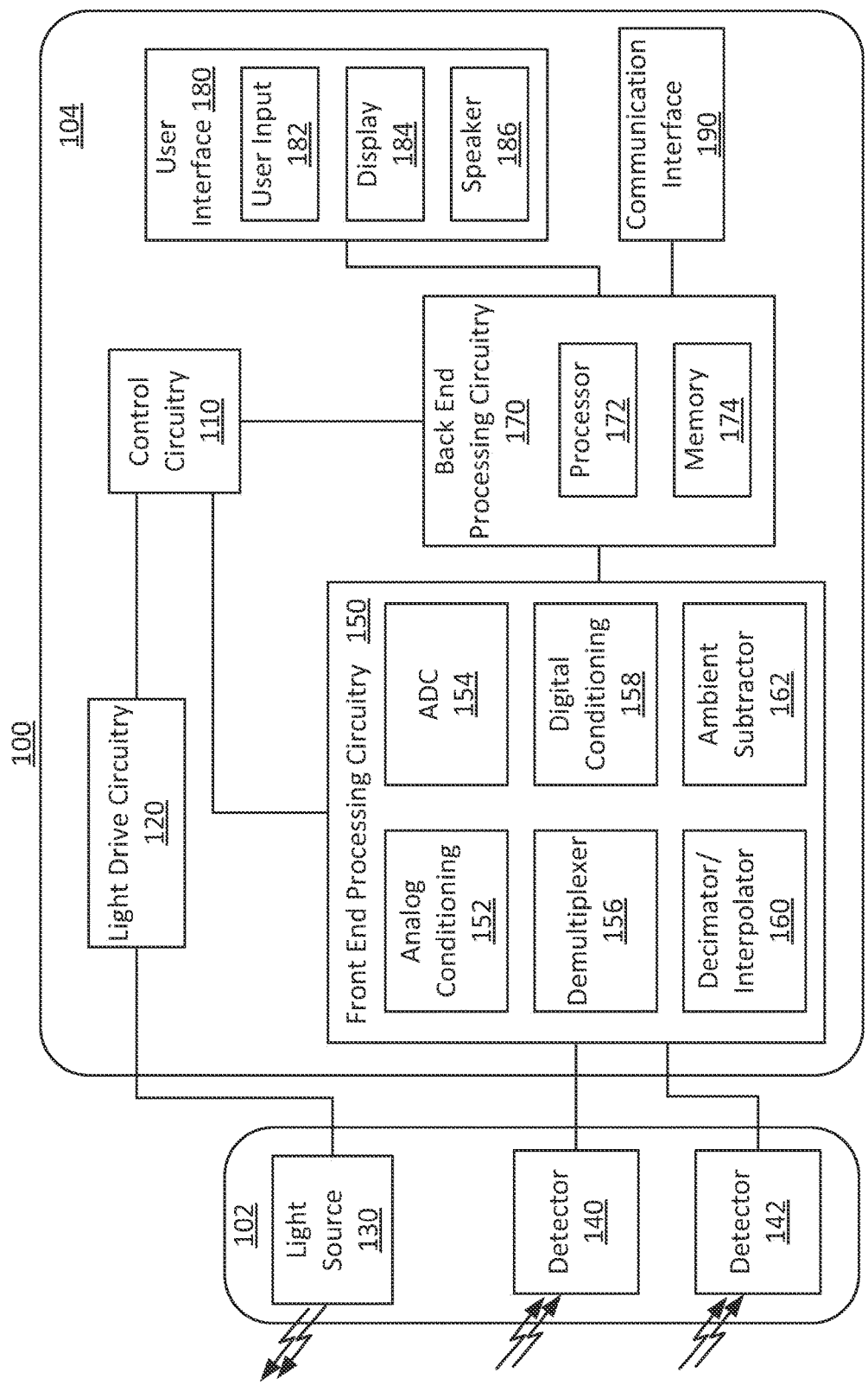
FIG. 1 is a block diagram of an illustrative physiological monitoring system in accordance with some embodiments of the present disclosure.

The present disclosure is directed towards determining whether a sensor is properly positioned on a subject. In some embodiments, the system of the present disclosure may be a regional oximetry system. First and second signals (e.g., PPG signals) may be received, the first signal representative of an intensity of light received at a first detector, and the second signal representative of an intensity of light received at a second detector. Metric values may be determined based on the first signal and on the second signal (e.g., a signal level of the first signal and a signal level of the second signal). A determination may be made as to whether the regional oximetry sensor is properly positioned on the subject based on the first metric value, the second metric value, and a relationship between the metrics.

In some embodiments, a first metric value and a second metric value are considered as pairs of metrics, and each pair of metrics is compared to a sensor-on region to determine whether the pair of metric falls within the sensor-on region. The sensor-on region may be based on a relationship between the first and second metrics. Pairs of metrics that fall within the sensor-on region may indicate that the regional oximetry sensor is properly positioned on the subject. In some embodiments, two or more metrics may be determined based on a plurality of received physiological signals. The two ore more metrics may be combined, using, for example, a neural network, to determine whether the regional oximetry sensor is properly positioned on a subject.

The foregoing techniques may be implemented in an oximeter. An oximeter is a medical device that may determine the oxygen saturation of an analyzed tissue. One common type of oximeter is a regional oximeter. A regional oximeter is used to estimate the blood oxygen saturation in a region of a subject's tissue. The regional oximeter may determine differences in the intensity of light received for each of two or more wavelengths of light received at two different locations on the subject's body (e.g., differential absorption values) to estimate the regional blood oxygen saturation of hemoglobin in a region of the subject's tissue. In some embodiments, the regional oximeter may, for each wavelength of light, compare the amount of light absorbed by the subject's tissue in a first region to the amount of light absorbed by the subject's tissue in a second region to derive differential absorption values. As opposed to pulse oximetry, which typically examines the oxygen saturation of pulsatile, arterial blood, regional oximetry examines the oxygen saturation of blood in a region of tissue that may include blood in the venous, arterial, and capillary system. For example, a regional oximeter may include a sensor unit configured for placement on a subject's forehead and may be used to estimate the blood oxygen saturation of a region of tissue beneath the sensor unit (e.g., cerebral tissue).

In some embodiments, the oximeter may be a combined oximeter including a regional oximeter and a pulse oximeter. A pulse oximeter is a device for non-invasively measuring the oxygen saturation of a patient's blood (as opposed to measuring oxygen saturation directly by analyzing a blood sample taken from the patient). Regional, pulse, and combined oximeters may be included in patient monitoring systems that measure and display various blood flow characteristics including, but not limited to, the regional oxygen saturation of a region of tissue and the oxygen saturation of hemoglobin in arterial blood. Such patient monitoring systems may also measure and display additional physiological parameters, such as a patient's pulse rate, respiration rate, respiration effort, blood pressure, any other suitable physiological parameter, or any combination thereof. Regional and pulse oximetry may be implemented using a photoplethysmograph. Pulse oximeters and other photoplethysmograph devices may also be used to determine other physiological parameters and information as disclosed in: J. Allen, "Photoplethysmography And its Application in Clinical Physiological Measurement," *Physiol. Meas.*, vol. 28, pp. R1-R39, March 2007; W. B. Murray and P. A. Foster, "The Peripheral Pulse Wave: Information Overlooked," *J. Clin. Monit.*, vol. 12, pp. 365-377, September 1996; and K. H. Shelley, "Photoplethysmography: Beyond the Calculation of Arterial Oxygen Saturation and Heart Rate," *Anesth. Analg.*, vol. 105, pp. S31-S36, December 2007; all of which are incorporated by reference herein in their entireties.

An oximeter may include a light sensor that is placed at a site on a patient, typically a fingertip, toe, forehead or earlobe, or in the case of a neonate, across a foot or hand. The oximeter may use a light source to pass light through blood perfused tissue and photoelectrically sense the absorption of the light in the tissue. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, around or in front of the ear, locations with strong pulsatile arterial flow, and locations above tissue desired to be monitored. Suitable sensors for these locations may include sensors that detect reflected light.

The oximeter may measure the intensity of light that is received at the light sensor as a function of time. The oximeter may also include sensors at multiple locations. A signal representing light intensity versus time or a mathematical manipulation of the signal (e.g., a scaled version thereof, a log taken thereof, a scaled version of log taken thereof, an inverted signal, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some embodiments, the photonic signal interacting with the tissue is of one or more wavelengths that are attenuated by the blood in an amount representative of the blood constituent concentration. In some embodiments, red and infrared (IR) wavelengths may be used because it has been observed that highly oxygenated blood will absorb relatively less red light and more IR light than blood with a lower oxygen saturation. In some embodiments, different infrared (IR) wavelengths may be used. By comparing the intensities of two wavelength at different points in the pulse cycle, it is possible to estimate the blood oxygen saturation of hemoglobin in arterial blood.

The system may process data to determine physiological parameters using techniques well known in the art. For example, the system may determine arterial blood oxygen saturation using two wavelengths of light and a ratio-of-ratios calculation. In another example, the system may determine regional blood oxygen saturation using multiple wavelengths of light and a differential absorption technique. The system also may identify pulses and determine pulse amplitude, respiration, blood pressure, other suitable parameters, or any combination thereof, using any suitable calculation techniques. In some embodiments, the system may use information from external sources (e.g., tabulated data, secondary sensor devices) to determine physiological parameters.

In some embodiments, the regional oximeter may include a first sensor located at a first distance from the light source (e.g., the near detector) and a second sensor located at a second farther distance from the light source (e.g., the far detector). In some embodiments, the regional oximeter may include a near detector at a distance of 3 centimeters (cm) and a far detector at a distance of 4 cm from the light source, which may include, for example, one or more emitters. The distance between each detector and the light source affects the mean path length of the detected light and thus the depth of tissue through which the respective received wavelength of light passes. In other words, the light detected by the near detector may pass through shallow, superficial tissue, whereas the light detected by the far detector may pass through additional, deep tissue. In some embodiments, the regional oximeter's light source may include two or more emitters and one or more detectors. For example, a first emitter may be located a short distance from a detector, and the second emitter may be located a longer distance from the detector.

In some embodiments, multiple wavelengths of light may be received at both the near and far detectors, and the absorption of the multiple wavelengths of light may be computed and contrasted at each detector to derive regional blood oxygen saturation. For example, light signals for four wavelengths of light may be received at each of the near and far detectors, and the amount of light of each wavelength received at the near detector may be subtracted from the amount of light of each wavelength received at the far detector. In some embodiments, the amount of absorption computed at the near detector for each wavelength may be subtracted from the corresponding amount of the absorption computed at the far detector. The resulting light signals or absorptions may be used to compute the regional blood oxygen saturation of a region of deep tissue through which light received at the far detector passed. Because the far detector receives light that passed through deep tissue in addition to the shallow tissue through which the light passes and is received at the near detector, the regional saturation may be computed for just the deep tissue by subtracting out the amount of light received by the near detector or the corresponding absorption. For example, a regional oximeter on a subject's forehead may include near and far detectors spaced from the light source such that the near detector receives light that passes through the subject's forehead tissue, including the superficial skin, shallow tissue covering the skull, and the skull, and the far detector receives light that passes through the forehead tissue and brain tissue (i.e., cerebral tissue). In the example, the differences in the amounts of light received by the near and far detectors may be used to derive an estimate of the regional blood oxygen saturation of the subject's cerebral tissue (i.e., cerebral blood oxygen saturation).

The following description and accompanying FIGS. 1-10 provide additional details and features of some embodiments of the present disclosure.

FIG. 1 is a block diagram of an illustrative physiological monitoring system 100 in accordance with some embodiments of the present disclosure. System 100 may include a sensor 102 and a monitor 104 for generating and processing physiological signals of a subject. In some embodiments, sensor 102 and monitor 104 may be part of an oximeter.

Sensor 102 of physiological monitoring system 100 may include light source 130, detector 140, and detector 142. Light source 130 may be configured to emit photonic signals having two or more wavelengths of light (e.g., red and IR) into a subject's tissue. For example, light source 130 may include a red light emitting light source and an IR light emitting light source, (e.g., red and IR light emitting diodes (LEDs)), for emitting light into the tissue of a subject to generate physiological signals. In one embodiment, the red wavelength may be between about 600 nm and about 700 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a red light while a second may emit only an IR light. In some embodiments, light source 130 may be configured to emit two or more wavelengths of near-infrared light (e.g., wavelengths between 600 nm and 1000 nm) into a subject's tissue. In some embodiments, light source 130 may be configured to emit four wavelengths of light (e.g., 724 nm, 770 nm, 810 nm, and 850 nm) into a subject's tissue.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detectors 140 and 142 may be chosen to be specifically sensitive to the chosen targeted energy spectrum of light source 130.

In some embodiments, detectors 140 and 142 may be configured to detect the intensity of multiple wavelengths of near-infrared light. In some embodiments, detectors 140 and 142 may be configured to detect the intensity of light at the red and IR wavelengths. In some embodiments, an array of sensors may be used and each sensor in the array may be configured to detect an intensity of a single wavelength. In operation, light may enter detector 140 after passing through the subject's tissue, including skin, bone, and other shallow tissue (e.g., non-cerebral tissue and shallow cerebral tissue). Light may enter detector 142 after passing through the subject's tissue, including skin, bone, other shallow tissue (e.g., non-cerebral tissue and shallow cerebral tissue), and deep tissue (e.g., deep cerebral tissue). Detectors 140 and 142 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 140 and 142. After converting the received light to an electrical signal, detectors 140 and 142 may send the detection signals to monitor 104, where the detection signals may be processed and physiological parameters may be determined (e.g., based on the absorption of the red and IR wavelengths in the subject's tissue at both detectors). In some embodiments, one or more of the detection signals may be preprocessed by sensor 102 before being transmitted to monitor 104. In some embodiments, sensor 102 may include additional sensors elements, such as additional light detectors or other types of sensor elements such as impedance detectors.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102 using, for example, one or more inputs.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate one or more light drive signals, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 120, as discussed above, may be configured to generate a light drive signal that is provided to light source 130 of sensor 102. The light drive signal may, for example, control the intensity of light source 130 and the timing of when light source 130 is turned on and off. In some embodiments, light drive circuitry 120 may comprise a power supply and a switch for selectively applying power to light source 130. When light source 130 is configured to emit two or more wavelengths of light, the light drive signal may be configured to control the operation of each wavelength of light. The light drive signal may comprise a single signal or may comprise multiple signals (e.g., one signal for each wavelength of light). In some embodiments, light drive circuitry 130 provides one or more light drive signals to light source 130.

Figure 2A:
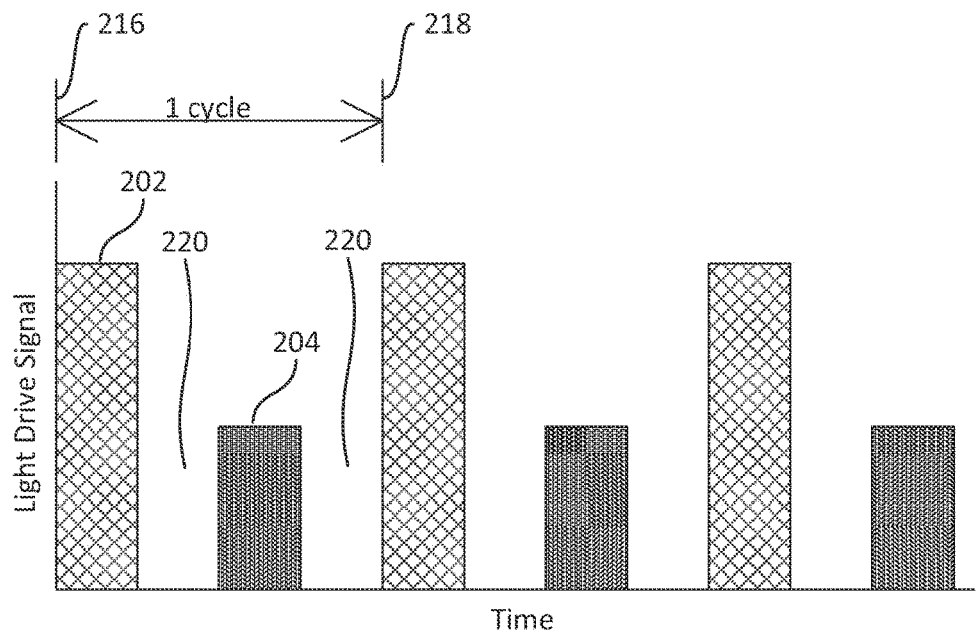
FIG. 2A shows an illustrative plot of a light drive signal in accordance with some embodiments of the present disclosure.

FIG. 2A shows an illustrative plot of a light drive signal including red light drive pulse 202 and IR light drive pulse 204 in accordance with some embodiments of the present disclosure. In the illustrated embodiment, light drive pulses 202 and 204 are shown as square waves. It will be understood that square waves are presented merely as an illustrative example, not by way of limitation, and that these pulses may include any other suitable signal, for example, shaped pulse waveforms, rather than a square waves. The shape of the pulses may be generated by a digital signal generator, digital filters, analog filters, any other suitable equipment, or any combination thereof. For example, light drive pulses 202 and 204 may be generated by light drive circuitry 120 under the control of control circuitry 110. As used herein, drive pulses may refer to the high and low states of a pulse, switching power or other components on and off, high and low output states, high and low values within a continuous modulation, other suitable relatively distinct states, or any combination thereof. The light drive signal may be provided to light source 130, including red light drive pulse 202 and IR light drive pulse 204 to drive red and IR light emitters, respectively, within light source 130.

Red light drive pulse 202 may have a higher amplitude than IR light drive 204 since red LEDs may be less efficient than IR LEDs at converting electrical energy into light energy. In some embodiments, the output levels may be equal, may be adjusted for nonlinearity of emitters, may be modulated in any other suitable technique, or any combination thereof. Additionally, red light may be absorbed and scattered more than IR light when passing through perfused tissue.

When the red and IR light sources are driven in this manner they emit pulses of light at their respective wavelengths into the tissue of a subject in order generate physiological signals that physiological monitoring system 100 may process to calculate physiological parameters. It will be understood that the light drive amplitudes of FIG. 2A are merely exemplary and that any suitable amplitudes or combination of amplitudes may be used, and may be based on the light sources, the subject tissue, the determined physiological parameter, modulation techniques, power sources, any other suitable criteria, or any combination thereof. It will also be understood that in systems that use more than two wavelengths of light, additional light drive pulses may be included in the light drive signal. For example, when four wavelengths of light are used, four light drive pulses, one for each wavelength of light, may be included in the light drive signal.

The light drive signal of FIG. 2A may also include "off" periods 220 between the red and IR light drive pulse. "Off" periods 220 are periods during which no drive current may be applied to light source 130. "Off" periods 220 may be provided, for example, to prevent overlap of the emitted light, since light source 130 may require time to turn completely on and completely off. The period from time 216 to time 218 may be referred to as a drive cycle, which includes four segments: a red light drive pulse 202, followed by an "off" period 220, followed by an IR light drive pulse 204, and followed by an "off" period 220. After time 218, the drive cycle may be repeated (e.g., as long as a light drive signal is provided to light source 130). It will be understood that the starting point of the drive cycle is merely illustrative and that the drive cycle can start at any location within FIG. 2A, provided the cycle spans two drive pulses and two "off" periods. Thus, each red light drive pulse 202 and each IR light drive pulse 204 may be understood to be surrounded by two "off" periods 220. "Off" periods may also be referred to as dark periods, in that the emitters are dark or returning to dark during that period. It will be understood that the particular square pulses illustrated in FIG. 2A are merely exemplary and that any suitable light drive scheme is possible. For example, light drive schemes may include shaped pulses, sinusoidal modulations, time division multiplexing other than as shown, frequency division multiplexing, phase division multiplexing, any other suitable light drive scheme, or any combination thereof.

Referring back to FIG. 1, front end processing circuitry 150 may receive detection signals from detectors 140 and 142 and provide two or more processed signals to back end processing circuitry 170. In some embodiments, front end processing circuitry 150 may receive the detection signals from one or more inputs of monitor 104. The term "detection signals," as used herein, may refer to any of the signals generated within front end processing circuitry 150 as it processes the output signal of detectors 140 and 142. Front end processing circuitry 150 may perform various analog and digital processing of the detector signals. One suitable detector signal that may be received by front end processing circuitry 150 is shown in FIG. 2B.

Figure 2B:
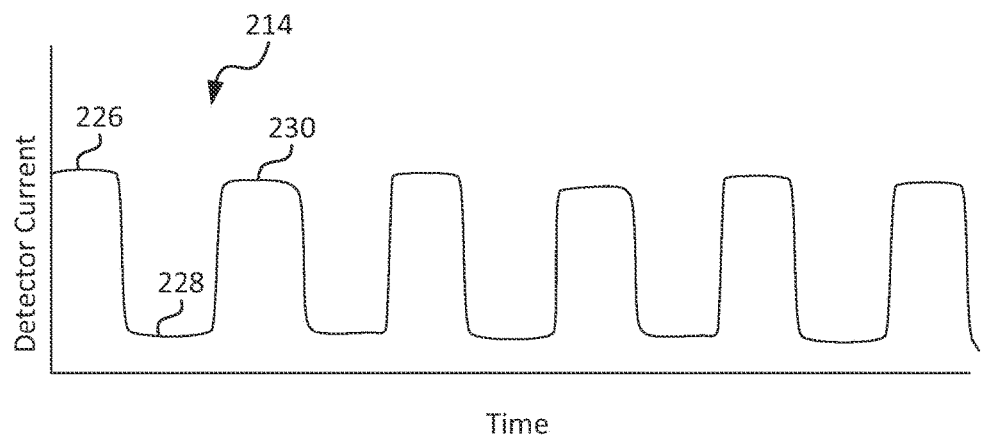
FIG. 2B shows an illustrative plot of a detector signal that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detectors 140 and 142 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current peak 226 may be generated in response to a light source being driven by red light drive pulse 202 of FIG. 2A, and peak 230 may be generated in response to a light source being driven by IR light drive pulse 204. Valley 228 of detector current waveform 214 may be synchronous with periods of time during which no light is being emitted by the light source, or the light source is returning to dark, such as "off" period 220. While no light is being emitted by a light source during the valleys, detector current waveform 214 may not fall all the way to zero.

It will be understood that detector current waveform 214 may be an at least partially idealized representation of a detector signal, assuming perfect light signal generation, transmission, and detection. It will be understood that an actual detector current will include amplitude fluctuations, frequency deviations, droop, overshoot, undershoot, rise time deviations, fall time deviations, other deviations from the ideal, or any combination thereof. It will be understood that the system may shape the drive pulses shown in FIG. 2A in order to make the detector current as similar as possible to idealized detector current waveform 214.

Referring back to FIG. 1, front end processing circuitry 150, which may receive detection signals, such as detector current waveform 214, may include analog conditioning 152, analog-to-digital converter (ADC) 154, demultiplexer 156, digital conditioning 158, decimator/interpolator 160, and ambient subtractor 162.

Analog conditioning 152 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., taking a derivative, averaging), performing any other suitable signal conditioning (e.g., converting a current signal to a voltage signal), or any combination thereof.

The conditioned analog signals may be processed by analog-to-digital converter 154, which may convert the conditioned analog signals into digital signals. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters. In some embodiments, analog-to-digital converter 154 may be a two channel analog-to-digital converter, where each channel is used for a respective detector waveform.

Demultiplexer 156 may operate on the analog or digital form of the detector signals to separate out different components of the signals. For example, detector current waveform 214 of FIG. 2B includes a red component corresponding to peak 226, an IR component corresponding to peak 230, and at least one ambient component corresponding to valley 228. Demultiplexer 156 may operate on detector current waveform 214 of FIG. 2B to generate a red signal, an IR signal, a first ambient signal (e.g., corresponding to the ambient component corresponding to valley 228 that occurs immediately after the peak 226), and a second ambient signal (e.g., corresponding to the ambient component corresponding to valley 228 that occurs immediately after the IR component 230). Demultiplexer 156 may operate under the control of control circuitry 110. For example, demultiplexer 156 may use timing control signals from control circuitry 110 to identify and separate out the different components of the detector signals.

Digital conditioning 158 may perform any suitable digital conditioning of the detector signals. Digital conditioning 158 may include any type of digital filtering of the signal (e.g., low pass, high pass, band pass, notch, averaging, or any other suitable filtering), amplifying, performing an operation on the signal, performing any other suitable digital conditioning, or any combination thereof.

Decimator/interpolator 160 may decrease the number of samples in the digital detector signals. For example, decimator/interpolator 160 may decrease the number of samples by removing samples from the detector signals or replacing samples with a smaller number of samples. The decimation or interpolation operation may include or be followed by filtering to smooth the output signal.

Ambient subtractor 162 may operate on the digital signal. In some embodiments, ambient subtractor 162 may remove dark or ambient contributions to the received signal.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signals by analog conditioning 152 to map the expected range of the detection signals to the full or close to full output range of analog-to-digital converter 154. The output value of analog-to-digital converter 154, as a function of the total analog gain applied to each of the detection signals, may be given as:

ADC Value=Total Analog Gain×[Ambient Light+ LED Light]

Ideally, when ambient light is zero and when the light source is off, the analog-to-digital converter 154 will read just above the minimum input value. When the light source is on, the total analog gain may be set such that the output of analog-to-digital converter 154 may read close to the full scale of analog-to-digital converter 154 without saturating. This may allow the full dynamic range of analog-to-digital converter 154 to be used for representing the detection signals, thereby increasing the resolution of the converted signal. In some embodiments, the total analog gain may be reduced by a small amount so that small changes in the light levels incident on the detectors do not cause saturation of analog-to-digital converter 154.

However, if the contribution of ambient light is large relative to the contribution of light from a light source, the total analog gain applied to the detection current may need to be reduced to avoid saturating analog-to-digital converter 154. When the analog gain is reduced, the portion of the signal corresponding to the light source may map to a smaller number of analog-to-digital conversion bits. Thus, more ambient light noise in the input of analog-to-digital converter 154 may result in fewer bits of resolution for the portion of the signal from the light source. This may have a detrimental effect on the signal-to-noise ration of the detection signals. Accordingly, passive or active filtering or signal modification techniques may be employed to reduce the effect of ambient light on the detection signals that applied to analog-to-digital converter 154, and thereby reduce the contribution of the noise component to the converted digital signal.

Back end processing circuitry 170 may include processor 172 and memory 174. Processor 172 may be adapted to execute software which may include an operating system and one or more applications, as part of performing the functions described herein. Processor 172 may receive and further process physiological signals received from front end processing circuitry 150. For example, processor 172 may determine one or more physiological parameters based on the received physiological signals. Processor 172 may include an assembly of analog or digital electronic components. Processor 172 may calculate physiological information. For example, processor 172 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof. In another example, processor 172 may compute metric values based on received physiological signals. Processor 172 may perform any suitable signal processing of a signal, such as any suitable band-pass filtering, adaptive filtering, closed-loop filtering, any other suitable filtering, and/or any combination thereof. Processor 172 may also receive input signals from additional sources not shown. For example, processor 172 may receive an input signal containing information about treatments provided to the subject from user interface 180. Additional input signals may be used by processor 172 in any of the calculations or operations it performs in accordance with back end processing circuitry 170 or monitor 104.

Memory 174 may include any suitable computer-readable media capable of storing information that can be interpreted by processor 172. In some embodiments, memory 174 may store relationship information, historical data, sensor information, sensor-on regions, metrics, metric values, calibration information, predetermined thresholds, calculated values, such as regional blood oxygen saturation, blood oxygen saturation, pulse rate, blood pressure, fiducial point locations or characteristics, initialization parameters, any other calculated values, or any combination thereof, in a memory device for later retrieval. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with user interface 180 and communication interface 190.

User interface 180 may include user input 182, display 184, and speaker 186. User interface 180 may include, for example, any suitable device such as one or more medical devices (e.g., a medical monitor that displays various physiological parameters, a medical alarm, or any other suitable medical device that either displays physiological parameters or uses the output of back end processing 170 as an input), one or more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth. The inputs received by user input 182 may also include information about the sensor, for example, the type or model of sensor, an indication of whether the sensor is an infant sensor or an adult sensor, an indication of where, on the subject, the sensor is configured for positioning, any other sensor specifications, or any combination thereof.

In an embodiment, the subject may be a medical patient and display 184 may exhibit a list of values which may generally apply to the subject, such as, for example, age ranges or medication families, which the user may select using user input 182. Additionally, display 184 may display, for example, a subject's regional oxygen saturation generated by monitor 104 (referred to as an "rSO$_2$" measurement), a subject's blood oxygen saturation generated by monitor 104 (referred to as an "SpO$_2$" measurement), an estimate of a subject's venous oxygen saturation generated by monitor 104 (referred to as an "S$_V$O$_Z$" measurement), sensor information, calibration information, metrics, sensor-on or sensor-off indications, pulse rate information, respiration rate information, blood pressure, any other parameters, and any combination thereof. Display 184 may include any type of display such as a cathode ray tube display, a flat panel display such a liquid crystal display (LCD), LED display, or plasma display, or any other suitable display device. Speaker 186 within user interface 180 may provide an audible sound that may be used in various embodiments, such as for example, sounding an audible alarm in the event that a patient's physiological parameters are not within a predefined normal range or in the event that the sensor is not properly positioned on the patient.

Communication interface 190 may enable monitor 104 to exchange information with external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, inputs, communications buses, communications protocols, device identification protocols, any other suitable hardware or software, or any combination thereof. Communications interface 190 may be configured to allow wired communication (e.g., using USB, RS-232, Ethernet, or other standards), wireless communication (e.g., using WiFi, IR, WiMax, BLUETOOTH, USB, or other standards), or both. For example, communications interface 190 may be configured using a universal serial bus (USB) protocol (e.g., USB 2.0, USB 3.0), and may be configured to couple to other devices (e.g., remote memory devices storing templates), using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In addition, while a single processor is depicted in FIG. 1, it will be understood that one or more processors may be used to perform the functionality described above. In other embodiments, the functionality of one or more of the components may be performed in a different order or may not be required. In an embodiment, all of the components of physiological monitoring system 100 can be realized in processor circuitry.

Figure 3:
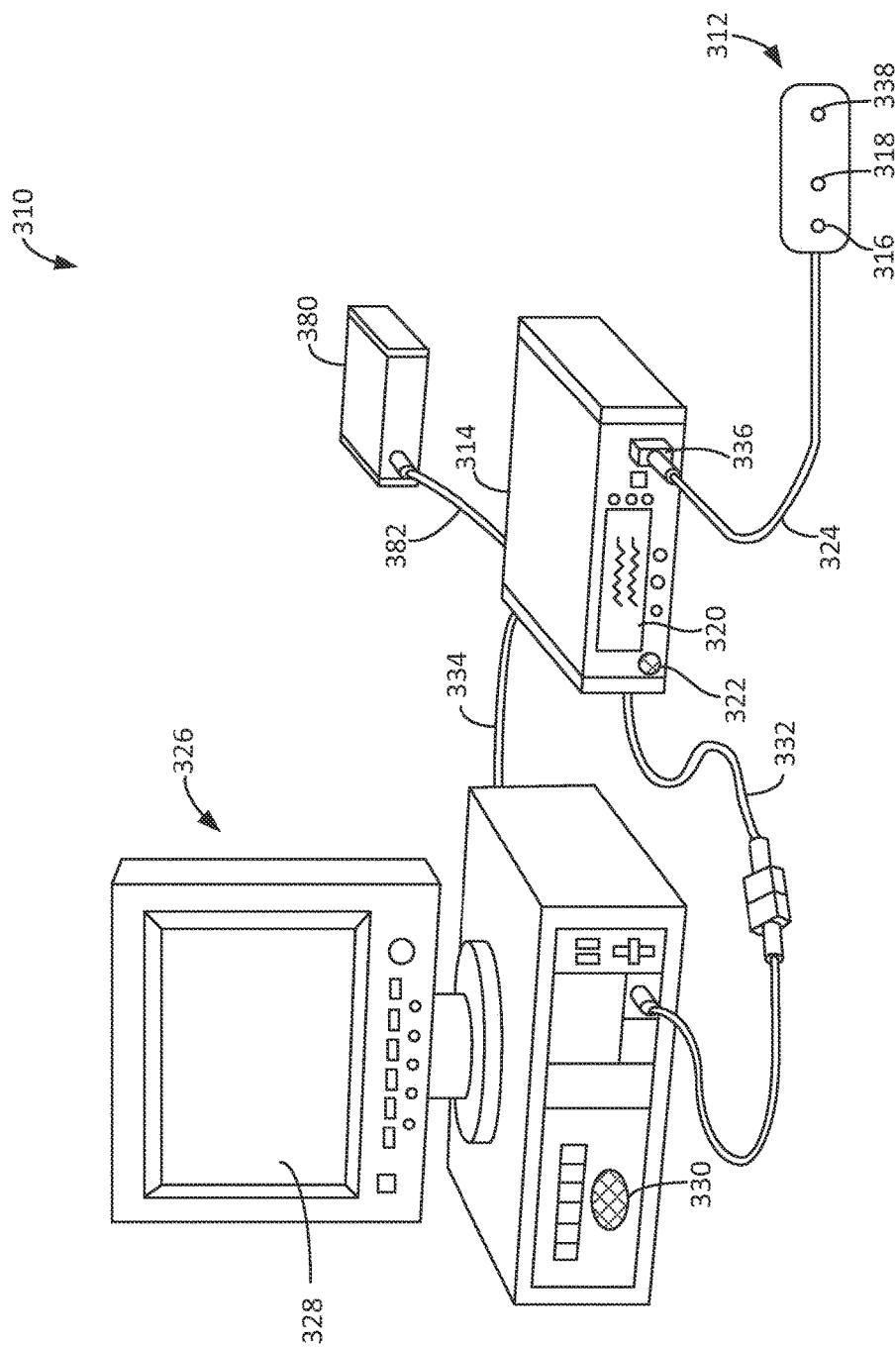
FIG. 3 is a perspective view of an illustrative physiological monitoring system in accordance with some embodiments of the present disclosure.

FIG. 3 is a perspective view of an illustrative physiological monitoring system 310 in accordance with some embodiments of the present disclosure. In some embodiments, one or more components of physiological monitoring system 310 may include one or more components of physiological monitoring system 100 of FIG. 1. Physiological monitoring system 310 may include sensor 312 and monitor 314. In some embodiments, sensor unit 312 may be part of an oximeter. Sensor unit 312 may include one or more light source 316 for emitting light at one or more wavelengths into a subject's tissue. Detectors 318 and 338 may also be provided in sensor unit 312 for detecting the light that is reflected by or has traveled through the subject's tissue. Any suitable configuration of light source 316 and detectors 318 and 338 may be used. In some embodiments, sensor unit 312 may include multiple light sources and detectors, which may be spaced apart. In some embodiments, detector 318 (i.e., the near detector) may be positioned at a location closer to light source 316 than detector 338 (i.e., the far detector). Physiological monitoring system 310 may also include one or more additional sensor units (not shown) that may, for example, take the form of any of the embodiments described herein with reference to sensor unit 312. An additional sensor unit may be the same type of sensor unit as sensor unit 312, or different sensor unit type than sensor unit 312 (e.g., a photoacoustic sensor). Multiple sensor units may be capable of being positioned at two different locations on a subject's body.

In some embodiments, sensor unit 312 may be connected to monitor 314 as shown. Sensor unit 312 may be powered by an internal power source, e.g., a battery (not shown). Sensor unit 312 may draw power from monitor 314. In another embodiment, the sensor may be wirelessly connected (not shown) to monitor 314. Monitor 314 may be configured to calculate physiological parameters based at least in part on data relating to light emission and acoustic detection received from one or more sensor units such as sensor unit 312. For example, monitor 314 may be configured to determine regional oxygen saturation, pulse rate, respiration rate, respiration effort, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 314. In some embodiments, monitor 314 may be configured to determine metric values based on received physiological signals (e.g., from sensor unit 312) and to determine whether a sensor is properly positioned on a subject based on the metric values and relationships between the metrics. Monitor 314 may also be configured to determine whether pairs of metric values fall within sensor-on regions. Further, monitor 314 may include display 320 configured to display the physiological parameters or other information about the system (e.g., an indication that the sensor is or is not properly positioned on a subject's tissue). In the embodiment shown, monitor 314 may also include a speaker 322 to provide an audible sound that may be used in various other embodiments, such as for example, sounding an audible alarm in the event that metric values do not fall within a sensor-on region. In some embodiments, physiological monitoring system 310 may include a stand-alone monitor in communication with the monitor 314 via a cable or a wireless network link. In some embodiments, monitor 314 may be implemented as monitor 104 of FIG. 1.

In some embodiments, sensor unit 312 may be communicatively coupled to monitor 314 via cable 324 at port 336. Cable 324 may include electronic conductors (e.g., wires for transmitting electronic signals from detectors 318 and 338), optical fibers (e.g., multi-mode or single-mode fibers for transmitting emitted light from light source 316), any other suitable components, any suitable insulation or sheathing, or any combination thereof. In some embodiments, a wireless transmission device (not shown) or the like may be used instead of or in addition to cable 324. Monitor 314 may include a sensor interface configured to receive physiological signals from sensor unit 312, provide signals and power to sensor unit 312, or otherwise communicate with sensor unit 312. The sensor interface may include any suitable hardware, software, or both, which may allow communication between monitor 314 and sensor unit 312.

In some embodiments, physiological monitoring system 310 may include calibration device 380. Calibration device 380, which may be powered by monitor 314, a battery, or by a conventional power source such as a wall outlet, may include any suitable calibration device. Calibration device 380 may be communicatively coupled to monitor 314 via communicative coupling 382, and/or may communicate wirelessly (not shown). In some embodiments, calibration device 380 is completely integrated within monitor 314. In some embodiments, calibration device 380 may include a manual input device (not shown) used by an operator to manually input reference signal measurements obtained from some other source (e.g., an external invasive or non-invasive physiological measurement system).

In the illustrated embodiment, physiological monitoring system 310 includes a multi-parameter physiological monitor 326. The monitor 326 may include a cathode ray tube display, a flat panel display (as shown) such as an LCD display, an LED display, or a plasma display, or may include any other type of monitor now known or later developed. Multi-parameter physiological monitor 326 may be configured to calculate physiological parameters and to provide a display 328 for information from monitor 314 and from other medical monitoring devices or systems (not shown). For example, multi-parameter physiological monitor 326 may be configured to display an indication as to whether a regional oximetry sensor unit (e.g., sensor unit 312) is properly positioned on a subject and the subject's regional blood oxygen saturation generated by monitor 314. In another example, multi-parameter physiological monitor 326 may be configured to display sensor information received from monitor 314 or from a sensor unit (not shown). Multi-parameter physiological monitor 326 may include a speaker 330.

Monitor 314 may be communicatively coupled to multi-parameter physiological monitor 326 via cable 332 or 334 that is coupled to a sensor input port or a digital communications port, respectively and/or may communicate wirelessly (not shown). In addition, monitor 314 and/or multi-parameter physiological monitor 326 may be coupled to a network to enable the sharing of information with servers or other workstations (not shown). Monitor 314 may be powered by a battery (not shown) or by a conventional power source such as a wall outlet.

In some embodiments, any of the processing components and/or circuits, or portions thereof, of FIGS. 1 and 3, including sensors 102 and 312 and monitors 104, 314, and 326 may be referred to collectively as processing equipment. For example, processing equipment may be configured to amplify, filter, sample and digitize input signals from sensor 102 or 312 (e.g., using an analog-to-digital converter), determine metrics from the input signals, and determine whether a sensor is properly positioned based on the metrics. The processing equipment may include one or more processors. In some embodiments, all or some of the components of the processing equipment may be referred to as a processing module or processing circuitry. In some embodiments, the processing equipment may be part of a regional oximetry system, and sensors 102 and 312 of FIGS. 1 and 3 may correspond to regional oximeter sensor unit 400 of FIG. 4, described below.

Figure 4:
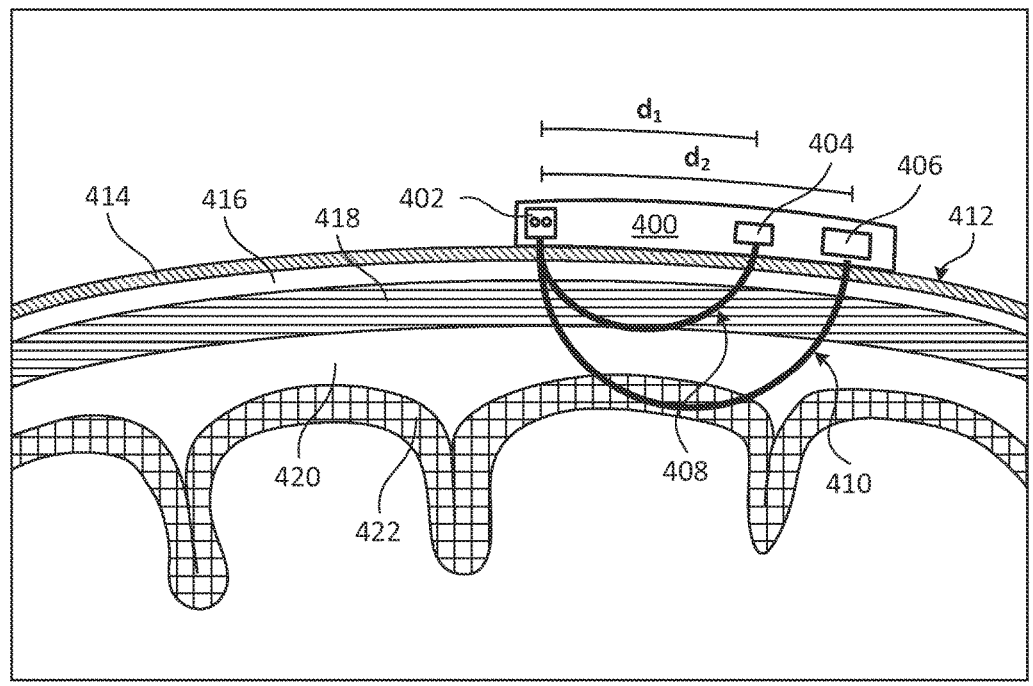
FIG. 4 is a cross-sectional view of an illustrative regional oximeter sensor unit applied to a subject's cranium in accordance with some embodiments of the present disclosure.

FIG. 4 is a cross-sectional view of an illustrative regional oximeter sensor unit 400 applied to a subject's cranium in accordance with some embodiments of the present disclosure. Regional oximeter sensor unit 400 includes light source 402, near detector 404, and far detector 406 and is shown as positioned on a subject's forehead 412. In the illustrated embodiment, light source 402 generated a light signal, which is shown traveling first and second mean path lengths 408 and 410 to respective near and far detectors 404 and 406. As shown, first and second mean path lengths 408 and 410 traverse the subject's cranial structure at different depths. The subject's cranial structure includes outer skin 414, shallow tissue 416, and cranial bone 416 (i.e., the frontal shell of the skull). Beneath cranial bone 416 is Dura Mater 420 and cerebral tissue 422.

In some embodiments, light source 402 of sensor unit 400 may include one or more emitters for emitting light into the tissue of a subject to generate physiological signals. Detectors 404 and 406 may be positioned on sensor unit 400 such that near detector 404 is located at distance $d_1$ from light source 402 and far detector 406 is located at a distance $d_2$ from light source 402. As shown, distance $d_1$ is shorter than distance $d_2$, and it will be understood that any suitable distances $d_1$ and $d_2$ may be used such that mean path length 408 of light detected by near detector 404 is shorter than the mean path length 410 of far detector 406. Near detector 404 may receive the light signal after it has traveled first mean path length 408, and far detector 406 may receive the light signal after it has traveled second mean path length 410. First mean path length 408 may traverse the subject's outer skin 414, shallow tissue 416, cranial bone 416, and Dura Mater 420. In some embodiments, first mean path length 408 may also traverse shallow cerebral tissue 422. Second mean path length 410 may traverse the subject's outer skin 414, shallow tissue 416, cranial bone 416, Dura Mater 420, and cerebral tissue 422.

In some embodiments, regional oximeter sensor unit 400 may be part of a regional oximetry system for determining the amount of light absorbed by a region of a subject's tissue. as described in detail above, light source 402 may emit multiple wavelengths of light (e.g., in the RED, the IR, or the RED and IR range of wavelengths of light) and for each wavelength of light, an absorption value may be determined based on the amount of light received at near detector 404, and an absorption value may be determined based on the amount of light received at far detector 406. For each wavelength of light, a differential absorption value may be computed based on the difference between the absorption values determined for near detector 404 and far detector 406. The differential absorption values may be representative of the amount of light absorbed by cerebral tissue 422 at each wavelength. Using known methods, the processing equipment may determine an $rSO_2$ value for a region of the subject's tissue based on the differential absorption values. In the illustrated embodiment, an $rSO_2$ value may be determined for a region of the subject's cerebral tissue 422. It will be understood that while the foregoing techniques for determining $rSO_2$ were described with reference to cerebral tissue, $rSO_2$ may be calculated for any suitable region of a subject's tissue. In some embodiments, the detected light signals may be normalized, for example, based on the amount of light emitted by light source 402, characteristics of the detectors, system gains, other suitable properties of the system, and/or empirical data prior to determining the absorption values.

In practice, a regional oximetry system may be used to monitor a subject's $rSO_2$ while the subject is undergoing a surgical procedure (e.g., cardiac surgery). During a cardiac surgical procedure, the heart may be stopped, and the laminar arterial blood flow may be maintained by a cardiac bypass machine. Thus, a PPG signal, generated by a regional oximetry system during this procedure, would reflect only the DC signal component (i.e., tissue, venous, and laminar/constant arterial flow) and not the pulsatile AC signal component (i.e., because the heart is not pumping blood. Hence, in this application, the regional oximetry system determines a subject's $rSO_2$ based only on the DC signal component. This can make it difficult to determine whether a sensor is properly positioned on a subject using conventional sensor-off techniques. For example, conventional sensor-off techniques cannot reliably distinguish between sensor application on human tissue or on an inanimate object. In accordance with the present disclosure, processing equipment may determine metrics, based on light intensity signals received at detectors of a regional oximetry sensor, and the metrics may provide information differentiating between sensor applications on tissue or off tissue. In some embodiments, the processing equipment may determine whether a sensor is properly positioned on a subject based on first and second metrics values and the relationship between the first and second metrics, as shown in FIG. 5.

FIG. 5 shows an illustrative flow diagram 500 including steps for determining whether a sensor is properly positioned on a subject in accordance with some embodiments of the present disclosure. The steps of flowchart 500 may be implemented as part of a regional oximetry system. The processing equipment may generate a light drive signal configured to cause one or more light sources to emit light corresponding to two or more wavelengths of light. The one or more light sources may correspond to light source 130 of FIG. 1, 316 of FIG. 3, or 402 of FIG. 4. In some embodiments, the one or more light sources may be part of a regional oximetry sensor. The light drive signal may correspond to the light drive signal shown in FIG. 2A.

At step 502, the processing equipment may receive first and second light signals. In some embodiments, the first signal is representative of an intensity of light received at a first detector of a regional oximetry sensor and the second light signal is representative of an intensity of light received at a second detector of the regional oximetry sensor. In some embodiments, the first and second light signals may each be representative of two or more wavelengths of light. It will be understood that light signals may be received at more than two detectors of a regional oximetry sensor. It will also be understood that the light signals may correspond to any suitable number of wavelengths of light. In some embodiments, the first and second signals may correspond to PPG signals. In some embodiments, the first signal may correspond to light that traveled a first mean path length to a first detector, and the second signal may correspond to light that traveled a second mean path length to a second detector. For example, the first and second signals may correspond to light that traveled respective mean path lengths 408 and 410 to respective near and far detectors 404 and 406 of FIG. 4. as described above, the first signal may correspond to light attenuated by a first region of tissue, and the second signal may correspond to light attenuated by a second region of tissue. In some embodiments, the first region may correspond to a smaller, shallow region of tissue than the second region, which may correspond to a larger, deep region of tissue. For example, the processing equipment may be implemented as part of a cerebral oximeter, where the first region may include the subject's outer skin, shallow tissue, cranial bone, Dura Mater, and shallow cerebral tissue and the second region may include all of the components of the first region and the subject's deeper cerebral tissue.

At step 504, the processing equipment may determine first and second metric values based on the received light signals.

In some embodiments, the first metric value is determined based on the first light signal and the second metric value is determined based on the second signal. In some embodiments, the processing equipment may determine first and second metric values based on processed first and second signals. For example, the processing equipment may normalize the first and second light signals before determining metric values. In some embodiments, the processing equipment may normalize the first and second signals based on respective first and second calibration coefficients. The signals may be normalized using any suitable processing equipment including, for example, processor 172 of FIG. 1, or monitor 314 or multi-parameter physiological monitor 326 of FIG. 3. In some embodiments, the processing equipment may determine the calibration coefficients based on at least one of the brightness of the light source, the sensitivity of the respective detector, system gains, other suitable properties of the processing equipment, and/or empirical data. In some embodiments, the processing equipment may determine a first calibration coefficient based on the brightness of the light source (e.g., light source 402 of FIG. 4) and the sensitivity of the first detector (e.g., near detector 404 of FIG. 4). In some embodiments, the processing equipment may determine a second calibration coefficient based on the brightness of the light source and the sensitivity of the second detector (e.g., far detector 406 of FIG. 4). It will be understood that more than one light source may be used, and the processing equipment may determine the calibration coefficients based on the brightness of the respective light source. In some embodiments, the processing equipment may receive calibration information from the sensor (e.g., regional oximeter sensor unit 400 of FIG. 4). Calibration information, as used herein, may include the sensitivity of each of the sensor's detectors, the brightness characteristics of each of the sensor's light sources, the wavelengths of light the sensor's light sources are configured to emit, the configuration of the light sources and detectors, any other suitable sensor characteristics, or any combination thereof. In some embodiments, the processing equipment may determine the first and second calibration coefficients based on the calibration information. For example, the processing equipment may received calibration information indicating the sensitivities of the first and second detectors and determine the first and second calibration coefficients based on the sensitivity of the respective detector.

In some embodiments, the first and second metrics may be associated with signal levels of the respective first and second signals. In some embodiments, the processing equipment may compute a first metric value as the logarithm of the first normalized signal and a second metric value as the logarithm of the second normalized signal. For example, the first metric value may correspond to the natural logarithm of an 810 nm wavelength component of the first normalized signal detected at a first detector positioned 30 mm from the light source, where the first signal is normalize to correct for variations in light source (e.g., LED) and detector efficiency. In another example, the second metric value may correspond to the natural logarithm of an 810 nm wavelength component of the second normalized signal detected at a second detector positioned 40 mm from the light source, where the second signal is normalized to correct for variations in light source (e.g., LED) and detector efficiency. In some embodiments, the processing equipment may detect variations in the levels of the first and second signals. In some embodiments, the processing equipment may determine first and second metric values based on the detected variations in the levels of the respective first and second signals. It will be understood that the processing equipment may determine any number of suitable metrics based on any number of suitable signals. For example, the processing equipment may determine a third metric value based on the first signal and a fourth metric value based on the second signal. In another example, the processing equipment may determine third and fourth metric values associated with one or more wavelength components of the first and second signals that are different from the one or more wavelength components used to determine the first and second metric values. It will be understood that each wavelength component of a signal may also be referred to herein as a signal.

In some embodiments, the processing equipment may determine first and second morphology metric values associated respectively with the morphology of the first and second signals. Morphology metrics, as used herein, may include suitable signal values, signal morphologies, output values from suitable operations performed on the signal or other metrics, any other suitable mathematical characterizations, or any suitable combinations thereof. For example, morphology metrics may include pulse wave area (PWA), geometric centroid of a pulse wave, rate of change computed at one or more points of a time series (e.g., derivative of any suitable order of a signal), statistics of a signal (e.g., mean, moment of any suitable order, regression parameters), offset of a signal from a baseline, interval of portion of a signal (e.g., length of upstroke), relative position of a fiducial point of a signal (e.g., dichrotic notch position), any other suitable metric or change thereof, or any suitable combinations thereof. In some embodiments, the processing equipment may determine a first morphology metric value based on the skewness (e.g., the standardized third central moment) of the first derivative of the first signal. In some embodiments, the processing equipment may determine a second morphology metric value based on the peak-to-peak modulation of the second signal. It will be understood that the processing equipment may determine any number of suitable morphology metrics associated with the morphologies of any number of suitable signals. For example, the processing equipment may determine a third morphology metric value associated with the morphology of the first signal and a fourth morphology metric value associated with the morphology of the second signal. In another example, the processing equipment may determine third and fourth morphology metric values associated respectively with the morphologies of third and fourth signals.

At step 506, the processing equipment may determine, based on the first and second metric values and a relationship between the first metric and the second metric, whether the regional oximetry sensor is properly positioned on the subject. In some embodiments, the relationship between the first and second metrics may be based on possible pairs of first and second metric values. In some embodiments, a relationship between first and second metrics may include any suitable mapping, pairing, association, or other suitable relationship between values of the first and second metrics such that it may be determined whether the sensor is properly positioned on the subject. For example, the relationship between first and second metrics may define values of the first metric and corresponding values of the second metric that fall within or define a sensor-on region. In some embodiments, the relationship between the first and second metrics may define a sensor-on region based on the possible pairs of first and second metric values. In some embodiments, the processing equipment may consider the first and second metric values as a pair of metrics and determine whether the pair of metrics falls within a sensor-on region, where the sensor-on region is determined based on a relationship between the first and second metrics. In some embodiments, the sensor-on region may be represented as a region in an x-y plane, where the x-axis is associated with a metric and the y-axis is associated with a metric. For example, the x-axis may correspond to values of the first metric, the y-axis may correspond to values of the second metric, and the sensor-on region may correspond to an area on the plot defined by a relationship between the first metric and the second metric. It will be understood that the representation of the sensor-region as a region in the x-y plane is merely illustrative and that a sensor-on region may correspond to a collection of data points, an array of metric values, data in a lookup table, ranges of metric values, any other suitable collection of values of metrics, or any combination thereof. In some embodiments, one metric may be used together with the relationship information to determine one or more thresholds or a range of values against which another metric is evaluated. For example, the first metric value may be used to determine the upper of and lower bounds of the sensor-on region for the second metric. The second metric may then be evaluated to determine whether it is between the upper and lower bounds to determine whether the sensor is properly positioned on the subject. In some embodiments, the processing equipment may determine a sensor-on region based on relationship information. In some embodiments, the processing equipment may receive relationship information from memory (e.g., memory 174 of FIG. 1), the sensor (e.g., regional oximeter sensor unit 400 of FIG. 4), or from a centralized information system (e.g., a hospital information system, any other suitable external source, or any combination thereof. As used herein, relationship information includes data indicative of any suitable relationship between metrics. In some embodiments, the processing equipment may receive relationship information based on historical data. In some embodiments, the processing equipment may determine a relationship between the first and second metrics based on historical data. Historical data may include, for example, historical calibration studies. In some embodiments, the historical data may include a plurality of first and second metric values recorded for sensors properly positioned to a plurality of subjects, and a relationship between the first and second metrics may be indicative of pairs of the first and second metric values associated with a sensor properly positioned to a subject. In some embodiments, the processing equipment may determine a sensor-on region based on a distribution of the historical data. For example, the historical data points may be plotted in the x-y plane, where the x-axis corresponds to values of the first metric, the y-axis corresponds to values of the second metric, and the processing equipment may determine the sensor-on region based on the distribution of the historical data points. In some embodiments, the processing equipment may receive relationship information that defines a sensor-on region, which may be represented in an x-y plane, and the processing equipment may determine whether pairs of first and second metric values fall within the sensor-on region.

Figure 6:
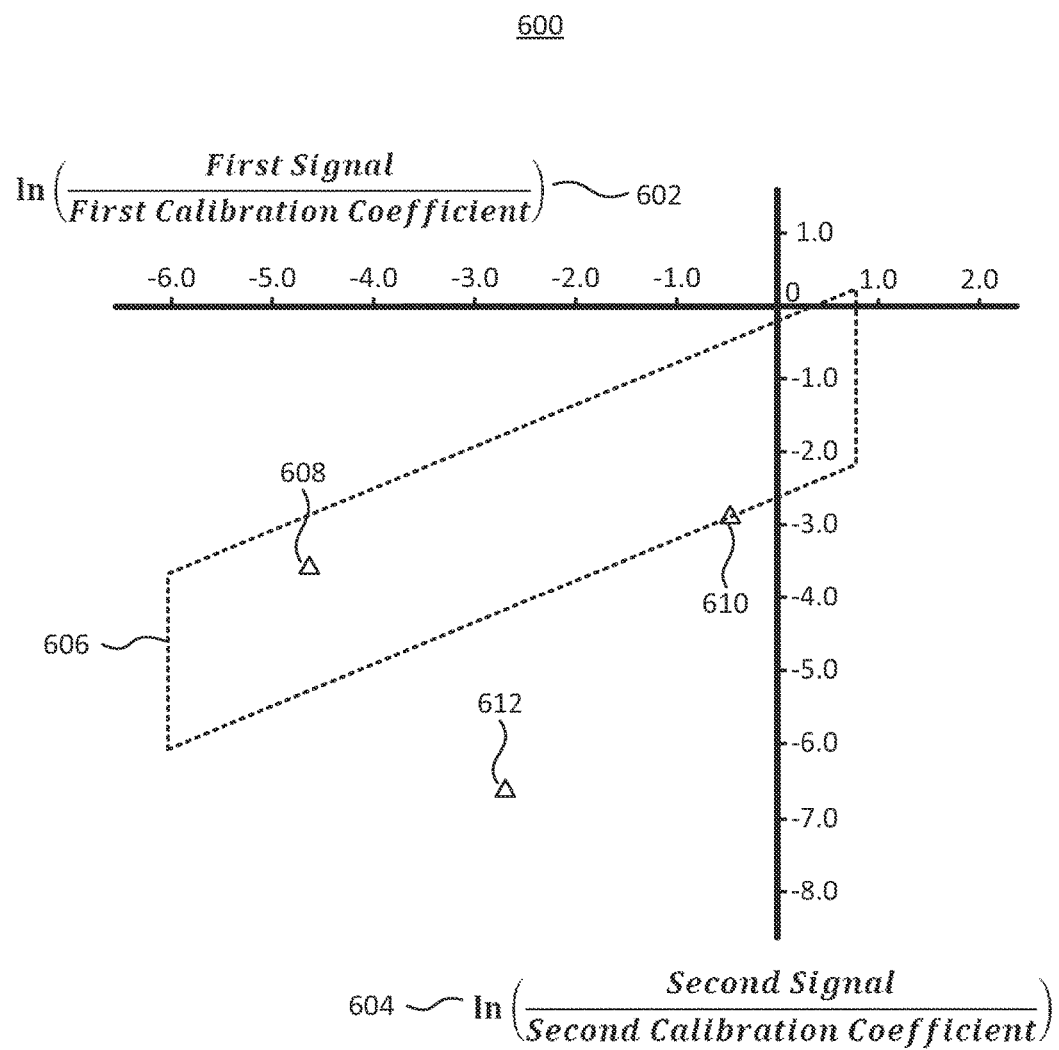
FIG. 6 shows an illustrative plot of a sensor-on region in accordance with some embodiments of the present disclosure.
Figure 7:
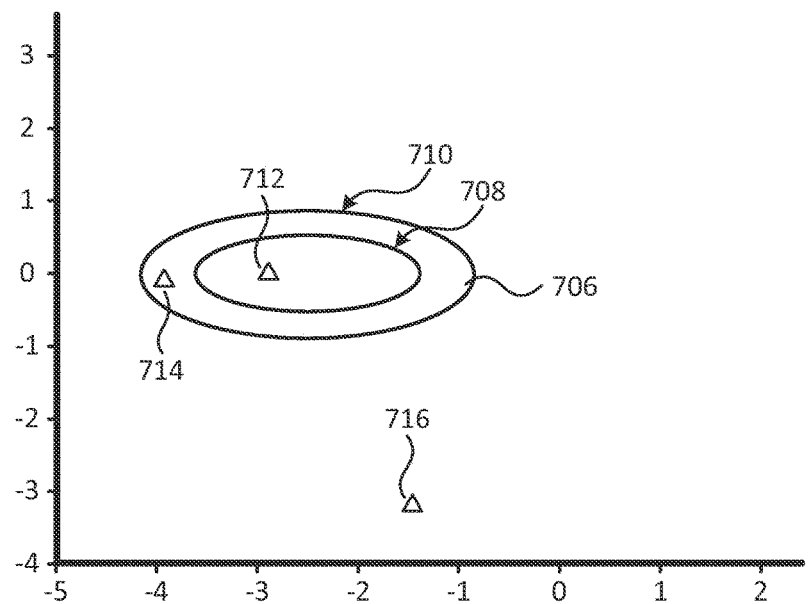
FIG. 7 shows an illustrative plot of a sensor-on region in accordance with some embodiments of the present disclosure.
Figure 8:
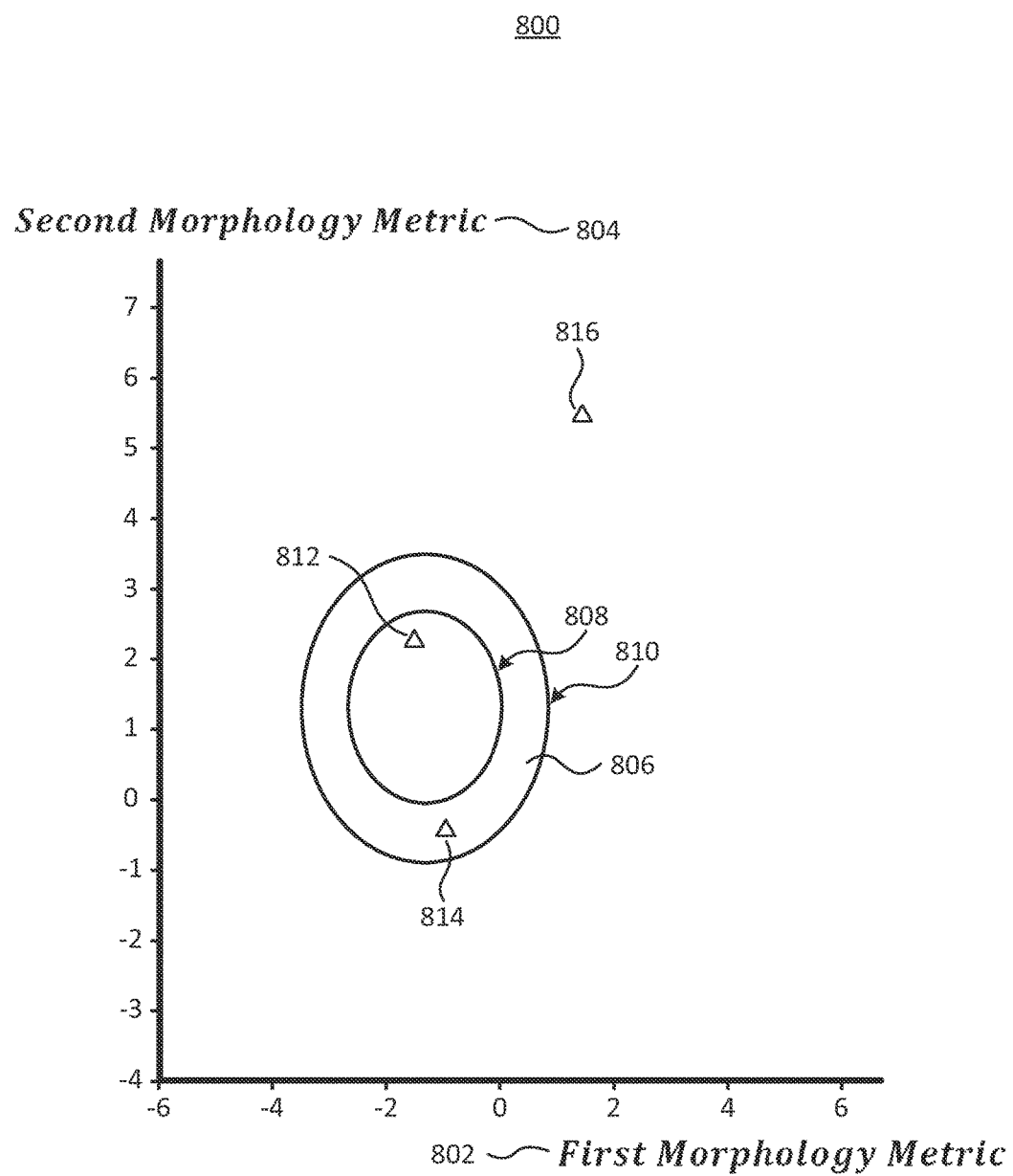
FIG. 8 shows an illustrative plot of a sensor-on region in accordance with some embodiments of the present disclosure.

FIGS. 6-8 show illustrative plots of sensor-on regions in accordance with some embodiments of the present disclosure. It will be understood that the particular plots shown, and the metrics of those plots, are merely exemplary. For purposes of brevity and clarity, and not by way of limitation, FIGS. 6-8 depict sensor-on regions as two-dimensional area in the x-y plane. It will be understood that, sensor-on regions are not limited to these depictions and may correspond to any suitable collections of data points, relationships, and number of metrics.

FIG. 6 shows an illustrative plot 600 of sensor-on region 606 in accordance with some embodiments of the present disclosure. The horizontal axis of plot 600 corresponds to first metric 602, and the vertical axis corresponds to second metric 604.

In some embodiments, the processing equipment may determine whether a sensor is properly positioned on a subject's tissue based on a first metric value, a second metric value, and a relationship between the first and second metrics (e.g., a sensor-on region). In some embodiments, the processing equipment may determine a first metric based on a first normalized signal and a second metric based on a second normalized signal. In some embodiments, the first and second signals may correspond to the first and second light signals described in step 502 of FIG. 5. For example, the first signal may correspond to an 810 nm wavelength component of light detected at a first detector positioned 30 mm from the light source, and the second signal may correspond to an 810 nm wavelength component of light detected at a second detector positioned 40 mm from the light source. As described above in reference to step 504 of FIG. 5, the processing equipment may normalize the first and second signals based on respective first and second calibration coefficients. In the embodiment shown, first metric 602 corresponds to the signal level of the first normalized signal, and second metric 604 corresponds to the signal level of the second normalized signal. First metric values $x_i$ are given by $$\ln\left(\frac{\text{First Signal}}{\text{First Calibration Coefficient}}\right), \quad (1)$$

and second metric values $y_i$ are given by $$\ln\left(\frac{\text{Second Signal}}{\text{Second Calibration Coefficient}}\right), \quad (2)$$

$i \in \mathbb{Z}^+$, $\mathbb{Z}^+$ denotes the set of positive integers, and the first and second calibration coefficients may be based on the brightness of the light source and the sensitivity of the respective first and second detectors, as described above with reference to step 504 of FIG. 5. In some embodiments, the sensor-on region 606, shown by a dashed line, may be based on a relationship between first metric 602 and second metric 604, such that pairs of metrics $(x_i, y_i)$ that fall within sensor-on region 606 may be indicative of a sensor properly positioned on a subject's tissue. For example, the processing equipment may determine a first metric value $x_1$ based on eq. 1 and a second metric value $y_1$ based on eq. 2. The processing equipment may consider the first and second metric values as a pair of metrics $(x_1, y_1)$, and determine if the pair of metrics $(x_1, y_1)$ falls within sensor-on region 606. In the example, pair of metrics $(x_1, y_1)$ may correspond to point 608, which the processing equipment may determine is within sensor-on region 606. In some embodiments, the processing equipment may determine that a sensor is properly positioned on a subject's tissue if a pair of first and second metric values is associated with a point inside the sensor-on region. In another example, the processing equipment may determine a first metric value $x_2$ on eq. 1 and a second metric value $y_2$ based on eq. 2, and the corresponding pair of metrics $(x_2, y_2)$ may correspond to point 612. In some embodiments, the processing equipment may determine that a sensor is not properly positioned on a subject's tissue if a pair of first and second metric values is associated with a point outside the sensor-on region. The processing equipment may determine that point 612 falls outside of sensor-on region 606. In some embodiments, the processing equipment may determine a pair of metric values corresponding to point 610, which is shown as falling on the edge of sensor-on region 606. In some embodiments, the processing equipment may determine that point 610 is within the sensor-on region, and in some embodiments, the processing equipment may determine that point 610 is outside of the sensor-on region. In some embodiments, the processing equipment may discard point 610 and determine a new pair of values for the first metric 602 and second metric 604. In some embodiments, first metric 602 and second metric 64 may correspond to variations in the levels of the respective first and second signals. In some embodiments, the processing equipment may determine whether a sensor is properly positioned on a subject's tissue based on combinations of metrics, as shown in FIG. 7.

FIG. 7 shows an illustrative plot 700 of sensor-on region 706 in accordance with some embodiments of the present disclosure. The horizontal axis and the vertical axis of plot 700 correspond to respective combination metrics 702 and 704. Sensor-on region 706 is depicted with two levels circumscribed by concentric ellipses 708 and 710.

In some embodiments, the processing equipment may determine whether a sensor is properly positioned on a subject's tissue based on non-linear combinations of metrics. In the embodiment shown, the processing equipment may determine combination metric 702 based on a combination of first metric 602 and second metric 604 of FIG. 6. In some embodiments, values of combination metric 702 are given by $$\text{First Metric} - \text{linreg}(\text{Second Metric}), \quad (3)$$

and values of metric 704 are give by $$\text{Second Metric} + 0.05*(\text{Second Metric})^2 \quad (4)$$

where "first metric" denotes first metric 602 of FIG. 6, "second metric" denotes second metric 604 of FIG. 6, and linreg denotes the linear regression operation. In some embodiments, eqs. 3 and 4 make take as input values of first metric 602 computed based on eq. 1, and values of second metric 604 computed based on eq. 2. In some embodiments, combination metric 702 make be indicative of the combined distribution of first metric 602 and second metric 604. In some embodiments, the processing equipment may determine values of combination metric 702 using eq. 3, which takes as input the linear regression of second metric 604 given by:

$$\text{linreg}(\text{Second Metric}) = m*\text{Second Metric} + b \quad (5)$$

where m and b denote linear regress coefficients, which may be empirically defined. In some embodiments, metric 704 may be indicative of the distribution of second metric 604. In some embodiments, the processing equipment may determine values of metric 704 using eq. 4, which includes a quadratic term $(0.05*(\text{Second Metric})^2)$ to compensate for the skewed distribution of second metric 604. In some embodiments, the processing equipment may determine whether a sensor is properly positioned on a subject's tissue based on combination metric 702, combination metric 704, and sensor-on region 706. In some embodiments, the processing equipment may determine combination metric 702 based on a near-infrared light component of the first signal and combination metric 704 based on a near-infrared light component of the second signal.

In some embodiments, the processing equipment may determine sensor-on region 706 based on the distribution of historical data, as described above in reference to step 506 of FIG. 5. In some embodiments, sensor-on region 706 may be partitioned into two levels, shown as ellipse 708 and ellipse 710. In some embodiments, ellipse 708 may correspond to two standard deviations from the center of the historical data distribution, and ellipse 710 may correspond to three standard deviations from the center of the historical data distribution. In some embodiments, the processing equipment may determine a value of combination metric 702 and a value of combination metric 704 as a pair of metrics associated with both of the first and second signals, as described above in connection with step of FIG. 5. The processing equipment may determine if the pair of metrics falls within sensor-on region 706. For example, the pair of metrics may correspond to point 712 of plot 700, which the processing equipment may determine is within sensor-on region 706, and more specifically, within ellipse 708 (i.e., within two standard deviations). In another example, the pair of metrics may correspond to point 714 of plot 700, which the processing equipment may determine is within sensor-on region 706, and more specifically, within ellipse 710 (i.e., within three standard deviations). In some embodiments, the processing equipment may determine that a sensor is properly positioned on a subject's tissue if a pair of metric values is associated with a point inside the sensor-on region. In another example, the pair of metrics may correspond to point 716 of plot 700, which the processing equipment may determine is not with sensor-on region 706. In some embodiments, the processing equipment may determine that a sensor is not properly positioned on a subject's tissue if a pair of first and second metric values is associated with a point outside the sensor-on region.

In some embodiments, the processing equipment may compare values of combination metrics 702 and 704 to a distribution threshold to determine whether a sensor is properly positioned on a subject's tissue. In some embodiments, the distribution threshold is a function of combination metrics 702 and 704, and the processing equipment may compare a value of combination metric 702 and a value of combination metric 704 to the distribution threshold. In some embodiments, the distribution threshold may be based on a function that circumscribes a two-dimensional sensor-on region, for example, sensor-on region 706 of plot 700. In some embodiments, the processing equipment may compare a value of combination metric 702 to a first distribution threshold and a value of combination metric 704 to a second distribution threshold and determine whether or not the pair of metrics falls within sensor-on region 706 based on the comparisons. For example, if the value of combination metric 702 exceeds the first distribution threshold, and the value of combination metric 704 does not exceed the second distribution threshold, then the processing equipment may determine that the pair of metrics does not fall within sensor-on region 706. In some embodiments, the processing equipment may determine more than one level of distribution threshold. For example, a first level distribution threshold may correspond to ellipse 708 and a second level distribution threshold may correspond to ellipse 710. The processing equipment may select and apply one of the plurality of thresholds based on the values of additional metrics or sensor characteristics, or may use the plurality of thresholds to control the display of user messages (e.g., deciding whether to display "sensor off" or "adjust sensor") and the timing thereof.

FIG. 8 shows an illustrative plot 800 of sensor-on region 806 in accordance with some embodiments of the present disclosure. The horizontal axis of plot 800 corresponds to first morphology metric 802, and the vertical axis corresponds to second morphology metric 804. Sensor-on region 806 is depicted with two levels circumscribed by concentric ellipses 808 and 810.

In some embodiments, the processing equipment may determine whether a sensor is properly positioned on a subject's tissue based on whether pairs of values of morphology metrics fall within a sensor-on region. In the embodiment shown, the processing equipment may determine a value of first morphology metric 802 and a value of second morphology metric 804. In some embodiments, the processing equipment may determine first morphology metric 802 based on a shape of the pulsatile modulation in a first signal. For example, a first morphology metric 802 may correspond to the shape of the pulsatile modulation in an 810 nm wavelength component of light detected at a first detector (e.g., detector 404 of FIG. 4) positioned 30 nm from the light source (e.g., light source 402 of FIG. 4). The processing equipment may use first morphology metric 802 to distinguish between the typical shape of a signal attenuated by a tissue site with pulsatile arterial blood as opposed to the shape of a signal attenuated by other non-tissue mediums. In some embodiments, the processing equipment may determine values of first morphology metric 802 based on the skewness (e.g., the standardized third central moment) of a derivative of the first signal. In some embodiments, the processing equipment may determine values of first morphology metric 802 by filtering the first signal using a highpass filter with a corner frequency of approximately 0.25 Hz, compressing the first signal's amplitude over a dynamic range based on the percent pulsatile modulation of the first signal to minimize the impact of large transient artifacts, and calculating the skewness of the first derivative of the compressed waveform. In some embodiments, the processing equipment does not subtract an ambient light estimate from the first signal before computing values of first morphology metric 802, because ambient light may be modulated by the pulsatile blood flow, and because the ambient light signal may add noise to the morphology calculation. It will be understood that while first morphology metric 802 has been described as determined based on a light signal received at the near detector, first morphology metric 802 may be determined based on any suitable signal, including the signal received at the far detector. The signal detected at the near detector has the advantage of being stronger than the signal detected at the far detector, so the processing equipment may determine a more accurate assessment of pulse shape based on the near signal. In some embodiments, the processing equipment may determine second morphology metric 804 based on a percentage modulation of a second signal. For example, second morphology metric 804 may correspond to the natural logarithm of the percentage of peak-to-peak pulsatile modulation of an 810 nm wavelength component of light detected at a detector (e.g., detector 406 of FIG. 4) positioned 40 mm from the light source (e.g., light source 402 of FIG. 4). In some embodiments, the processing equipment may compute the peak-to-peak modulation of the second signal as:

$$\frac{\text{Amplitude}_{max} - \text{Amplitude}_{min}}{\text{Average Amplitude}}, \quad (6)$$

where the amplitude values are computed over a 1 second window. The processing equipment may then average the output of eq. 6 over a 4 second window. The processing equipment may use second morphology metric 804, computed using eq. 6, to distinguish pulse amplitudes that are typical of a signal attenuated by a tissue site with pulsing arterial blood as opposed to a "flat line" (i.e., no pulsatile modulation) or large transient amplitudes associated with sensor manipulation (e.g., artifact).

In some embodiments, the processing equipment may determine sensor-on region 806 based on the distribution of historical data, as described above in reference to step 506 of FIG. 5. In some embodiments, sensor-on region 806 may be partitioned into two levels, shown as ellipse 808 and ellipse 810. In some embodiments, ellipse 808 may correspond to two standard deviations from the center of the historical data distribution, and ellipse 810 may correspond to three standard deviations from the center of the historical data distribution. In some embodiments, the processing equipment may determine a value of first morphology metric 802 and a value of second morphology metric 804 and consider the values as a pair of metrics associated with the morphologies of respective first and second signals, as described above in connection with step 506 of FIG. 5. The processing equipment may determine if the pair of metrics falls within sensor-on region 806. For example, the pair of metrics may correspond to point 812 of plot 800, which the processing equipment may determine is with sensor-on region 806, and more specifically, within ellipse 808 (i.e., within two standard deviations). In another example, the pair of metrics may correspond to point 814 of plot 800, which the processing equipment may determine is within sensor-on region 806, and more specifically, within ellipse 810 (i.e., within three standard deviations). In some embodiments, the processing equipment may determine that a sensor is properly positioned on a subject's tissue if a pair of metric values is associated with a point inside the sensor-on region. In another example, the pair of metrics may correspond to point 816 of plot 800, which the processing equipment may determine is not within sensor-on region 806. In some embodiments, the processing equipment may determine that a sensor is not properly positioned on a subject's tissue if a pair of first and second morphology metric values is associated with a point outside the sensor-on region.

It will be understood that the particular plots shown in FIGS. 6-8 are merely exemplary and are presented as non-limiting illustrations. For example, it will be understood that any suitable combination of individual metrics, combination metrics, and morphology metrics may be used to determine whether a sensor is properly positioned.

FIG. 9 shows an illustrative flow diagram 900 including steps for determining whether a sensor is properly positioned on a subject in accordance with some embodiments of the present disclosure. The steps of flowchart 900 may be implemented as part of a regional oximetry system. The processing equipment may include one or more light sources for emitting a plurality of wavelengths of light. The one o more light sources may correspond to light source 130 of FIG. 1, 316 of FIG. 3, or 402 of FIG. 4. In some embodiments, the one or more light sources may be part of a regional oximetry sensor.

At step 902, the processing equipment may receive a plurality of physiological signals. In some embodiments, step 902 may correspond to step 502 of FIG. 5. As described above, the processing equipment may receive a plurality of physiological signals at first and second detectors of a regional oximetry sensor. In some embodiments, the physiological signals may be representative of an intensity of light received at a respective detector. In some embodiments, the physiological signals may correspond to PPG signals.

At step 904, the processing equipment may receive sensor information. In some embodiments, the processing equipment may receive sensor information from the monitor memory (e.g., memory 174 of FIG. 1), the sensor (e.g., regional oximeter sensor unit 400 of FIG. 4, or from a centralized information system (e.g., a hospital information system), any other suitable external source, or any combination thereof. Sensor information, as used herein, may include the type or mode of sensor, an indication of whether the sensor is an infant sensor or an adult sensor, an indication of where, on the subject, the sensor is configured for positioning, any other sensor specifications, or any combination thereof. For example, the processing equipment may receive sensor information indicating that the sensor is an infant sensor configured for positioning on an infant's forehead (i.e., a cerebral oximeter).

At step 906, the processing equipment may determine a plurality of metrics based on the plurality of physiological signals. In some embodiments, step 906 may correspond to step 504 of FIG. 5. As described above, in some embodiments, the processing equipment may determine first and second metrics based respectively on first and second physiological signals. In some embodiments, the processing equipment may determine a plurality of metrics based on the first signal and a plurality of metrics based on the second signal. In some embodiments, the processing equipment may receive three physiological signals (e.g., representative of intensities of light received at three detectors) and determine a first metric based on the first signal, a second metric based on the second signal, and a third metric based on the third signal. In some embodiments, the processing equipment may determine a plurality of metrics for each of a plurality of physiological signals. For example, the processing equipment may determine a plurality of metrics for each of first, second, and third physiological signals.

In some embodiments, as described above in reference to step 504 of FIG. 5, the processing equipment may determine first and second morphology metric values associated respectively with the morphologies of first and second physiological signals. For example, the processing equipment may determine a first morphology metric value based on the shape of the pulsatile modulation of the first signal (e.g., shallow signal traveling mean path length 408 to near detector 404 of FIG. 4). In another example, the first morphology metric value may be determined based on the skewness of a first derivative of the first signal. In another example, the processing equipment may determine a second morphology metric value based on the peak-to-peak modulation of the second signal (e.g., deep signal traveling mean path length 410 to far detector 406 of FIG. 6). In some embodiments, the processing equipment may determine a plurality of morphology metrics associated with a plurality of physiological signals.

In some embodiments, the processing equipment may determine any number of additional metrics based on the received physiological signals. Additional metrics may include, for example, ambient light levels, pulse (AC) amplitudes and shapes, large transient variations in signal levels correlations between pulsatile parts of any two emitter/detector pairs, the history of any metrics during a monitoring session, the history of the sensor-off assessment (e.g., hysteresis), metrics based on non-optical signals (e.g., a metric based on an impedance signal), any other suitable metrics, or any combination thereof. In some embodiments, the processing equipment may determine a metric value based on an ambient light component of a received physiological signal. For example, the processing equipment may determine an ambient light metric value based on the natural logarithm of the ambient light component of a light signal received at a detector positioned 40 mm from a light source on a regional pulse oximetry sensor (e.g., regional oximetry sensor unit 400 of FIG. 4). In some embodiments, a second ambient light metric value may be derived from the ambient light received at a detector position 30 mm from the light source. In some embodiments, the processing equipment may determine the ambient light metric value when the light source is off. In some embodiments, the processing equipment may determine a first trend parameter based on the values of a first metric over time and a second trend parameter based on the values of a second metric over time. For example, the processing equipment may determine first and second trend parameters based respectively on the values of first and second metrics over time, where the first and second metrics are based respectively on the signal levels of first and second normalized signals (e.g., first metric 602 and second metric 604 of FIG. 6). In some embodiments, the processing equipment may detect variations in the levels of first and second signals and determine respective first and second metric values based on the detected signal level variations. It will be understood that while physiological signals have been discussed as corresponding to light signals, this is merely illustrative, not limiting, and the processing equipment may determine metric values based on any suitable physiological signals. In some embodiments, the processing equipment may receive an impedance signal and determine a metric value based on the impedance signal.

At step 908, the processing equipment may determine, based on the plurality of metrics and/or the sensor information, whether a sensor is properly positioned on a subject. In some embodiments, step 908 may correspond to step 506 of FIG. 5. In some embodiments, the processing equipment may combine the plurality of metric values and the sensor information to determine whether the sensor is properly positioned on the subject. In some embodiments, the plurality of metrics may correspond to the plurality of metric values determined in step 906, and the sensor information may correspond to the sensor information received in step 904. For example, the processing equipment may determine whether the sensor is properly positioned on the subject based on first and second metric values based respectively on the signal levels of first and second normalized signals, a third metric value based on an impedance signal, an ambient light metric based on the ambient light component of the second signal, first and second morphology metrics based respectively on the morphologies of the first and second signals, and the sensor information. The sensor information may include, for example, a sensor type identifying whether the regional oximetry sensor is an infant sensor or an adult sensor, an indication of how well the sensor shields the detectors from ambient light, and/or sensor information indicative of where, on the subject, the regional oximetry sensor is configured for positioning. In some embodiments, the processing equipment may determine whether pairs of the plurality of metrics fall within respective sensor-on regions, where the sensor-on regions are associated with a relationship between the paired metrics. For example, the processing equipment may determine whether a pair of values of signal level metrics (e.g., metrics 602 and 604 of FIG. 6) falls within a sensor-on region (e.g., sensor-on region 606 of FIG. 6). In some embodiments, the processing equipment may assign a score to the pair of metrics based on whether or not it falls within the sensor-on region (e.g., a score of "0" for "yes" and "1" for "no"). In another example, the processing equipment may determine a score of "2" for a pair of metrics that is determined to fall within two standard deviations (e.g., ellipse 708 of FIG. 7, ellipse 808 of FIG. 8) of the center of a distribution sensor-on region and a score of "3" for a pair of metrics falling within three standard deviations (e.g., ellipse 710 of FIG. 7, ellipse 810 of FIG. 8). In some embodiments, the processing equipment may assign a score to each of the plurality of metrics determined in step 906. For example, the processing equipment may assign a score of "0" to metrics indicating the sensor is properly positioned and a "1" to metrics indicating the sensor may not be properly positioned. The processing equipment may combine the assigned scores using an average, a weighted average (e.g., pairs associated with points partially inside and partially outside of a sensor-on region may be weighed heavier), a summation, any other suitable technique for combining the scores to form a combined score, or any combination thereof. In some embodiments, the processing equipment may determine that a sensor is not properly positioned on the subject of a tissue if the combined score exceeds a threshold. In some embodiments the processing equipment may determine that a sensor is not properly positioned on a subject's tissue if any of the metrics is indicative of an improper position or any of the pairs of metrics fall outside a sensor region. In some embodiments, the processing equipment may determine that a sensor is properly positioned on a subject's tissue if a majority of the metrics and pairs of metrics are indicative of a properly positioned sensor. In some embodiments, the processing equipment may combine the plurality of metrics and the sensor information using a neural network, as shown in FIG. 10.

Figure 10:
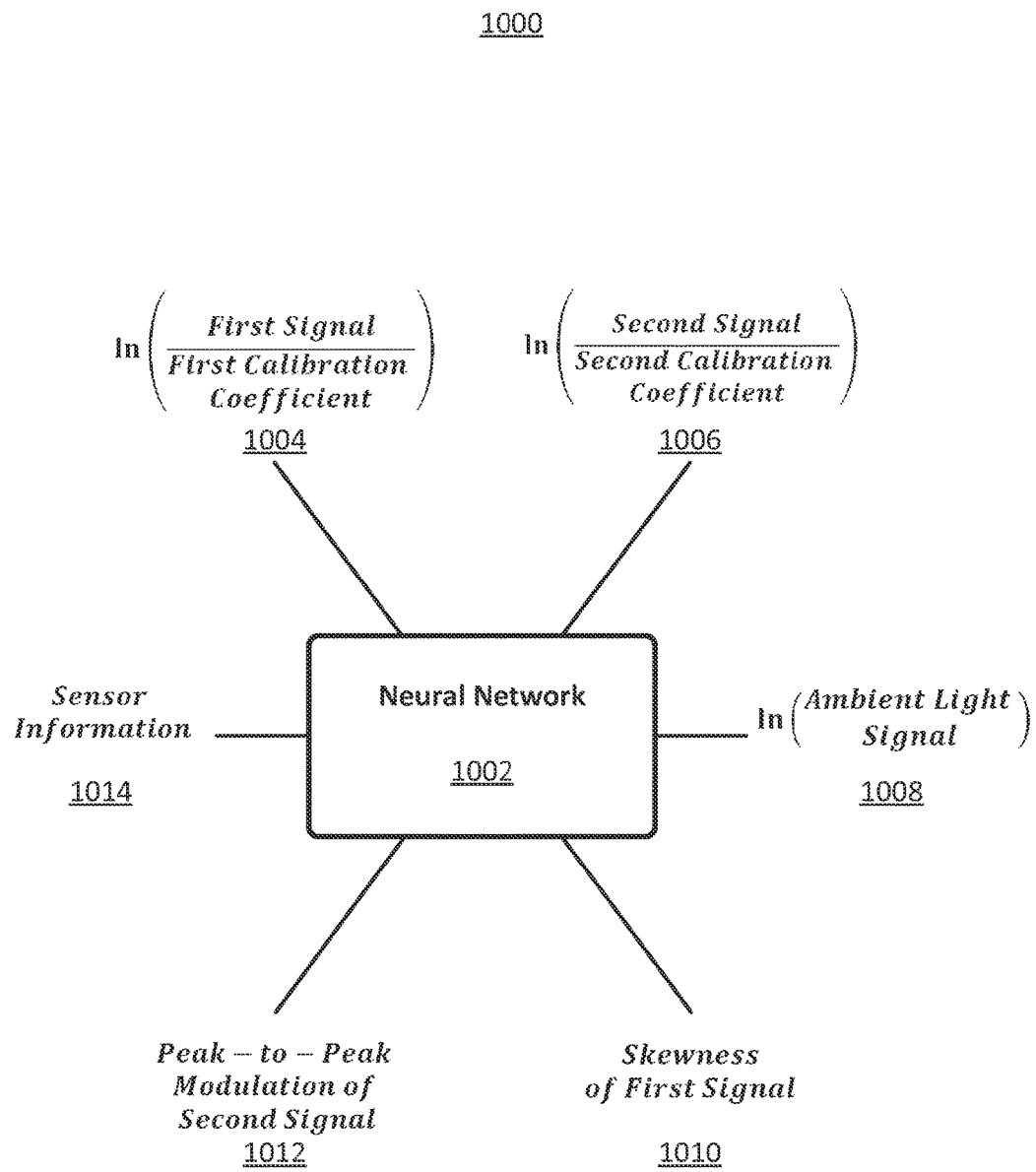
FIG. 10 shows an illustrative block diagram for determining whether a regional oximetry sensor is properly positioned on a subject using a neural network in accordance with some embodiments of the present disclosure.

FIG. 10 shows an illustrative block diagram 1000 for determining whether a regional oximetry sensor is properly positioned on a subject using a neural network in accordance with some embodiments of the present disclosure. Neural network 1002 may be implemented using any suitable processing equipment including, for example, processor 172 of FIG. 1. In some embodiments, neural network 1002 may be trained empirically, using historical data or training data indicative of sensors properly positioned on tissue and sensors positioned on non-tissue. In some embodiments, neural network 1002 may be trained using two or more detectors, and each detector may have a different degree of sensitivity to ambient light. In some embodiments, neural network 1002 may be trained using a Levenberg-Marquardt training method. In some embodiments, neural network 1002 may be a fully inter-connected, feed-forward neural network, including eight nodes in a single hidden layer and a logarithmic sigmoid transfer function. In some embodiments, neural network 1002 may receive inputs that have been calculated over a 64-sample window (e.g., corresponding to 4-5 seconds).

In some embodiments, neural network 1002 may input the plurality of metrics determined in step 906. In the embodiment shown, neural network 1002 may input metric values 1004-1012 and sensor information 1014. In some embodiments, metrics 1004 and 1006 may correspond to first and second metrics 602 and 604 of FIG. 6 metric 1008 may correspond to ambient light metric determined in step 906 above, metrics 1012 and 1010 may correspond to first and second morphology metrics 802 and 804 of FIG. 8, and sensor information 1014 may correspond to the signal information received in step 904 above. In some embodiments, neural network 1002 may determine, based on input metrics 1004-1012 and/or sensor information 1014 whether a sensor is properly positioned on a subject. In some embodiments, neural network 1002 may combine input metrics 1004-1012 and/or sensor information 1014 to determine whether the sensor is properly positioned on the subject. It will be understood that neural network 1002 is provided as an illustrative example, not by way of limitation, and that any suitable processing module or technique may be used to combine the metrics, including, for example, state machines, fuzzy logic techniques, Bayesian logic techniques, Markov models, evolutionary/genetic algorithms, any other suitable processing technique or module, or an combination thereof.

Referring back to FIG. 9, at step 910, the processing equipment may determine the $rSO_2$ of a region of the subject's tissue when it is determined that the sensor is properly positioned on the subject. In some embodiments, the $rSO_2$ value may be displayed on display 184 of FIG. 1, display 328 of multi-parameter physiological monitor 326 or display 320 of monitor 314 of FIG. 3, or any other suitable display for depicting physiological information. In some embodiments, when it is determined that the regional oximetry sensor is not properly positioned on the subject, the processing equipment may display a sensor off message. In some embodiments, the processing equipment may sound an audible alarm using, for example, speaker 186 of FIG. 1. In some embodiments, the processing equipment may not display a sensor off message or an $rSO_2$ value. In some embodiments, the processing equipment may include other messages or indicators.

It will be understood that the steps above are exemplary and that in some implementations, steps may be added, removed, omitted, repeated, reordered, modified in any other suitable way, or any combination thereof. For example, in some embodiments, step 904 may be omitted, and at step 908, the processing equipment may determine based on the plurality of metrics whether the sensor is properly positioned on a subject.

It will be understood that noise, such as motion artifact, may cause instantaneous metric values to fall outside of a sensor-on region even though the sensor is properly positioned. In order to prevent false determinations of sensor off, the determination of whether a sensor is properly positioned (e.g., at step 506 of FIG. 5 and step 908 of FIG. 9) may include additional processing steps. For example, the metric values may be averaged over time to prevent short-term deviations due to noise from causing a sensor off determination. As another example, a sensor off determination may be declared after the metrics fall outside of a sensor-on region for a predetermined continuous amount of time. These examples are merely illustrative and any suitable techniques may be used to prevent false determinations of sensor off.

The foregoing is merely illustrative of the principles of this disclosure, and various modifications may be made by those skilled in the art without departing from the scope of this disclosure. The above-described embodiments are presented for purposes of illustration and not by way of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A system comprising:
   one or more inputs configured to:
      receive a first signal representative of an intensity of light at a first detector of a regional oximetry sensor, and
      receive a second signal representative of an intensity of light at a second detector of the regional oximetry sensor; and
   one or more processors configured to:
      determine a first metric value based on the first signal;
      determine a second metric value based on the second signal;
      determine a first combination metric value based on the first metric value and the second metric value;
      determine a second combination metric value based on the second metric value, and
      determine, based on the first combination metric value and the second combination metric value, that the regional oximetry sensor is properly positioned relative to a target site on a subject.

2. The system of claim 1, wherein the one or more processors are configured to determine that the regional oximetry sensor is properly positioned relative to the target site by at least comparing the first combination metric value and the second combination metric value to a distribution threshold.

3. The system of claim 1, wherein the one or more processors are configured to determine that the regional oximetry sensor is properly positioned relative to the target site by at least comparing the first combination metric value to a first distribution threshold and comparing the second combination metric value to a second distribution threshold.

4. The system of claim 3, wherein the one or more processors are configured to determine that the regional oximetry sensor is properly positioned relative to the target site in response to determining that the first combination metric value exceeds the first distribution threshold and that the second combination metric does not exceed the second distribution threshold.

5. The system of claim 1, wherein the one or more processors are configured to use a neural network to determine, based on the first combination metric value and the second combination metric value, that the regional oximetry sensor is properly positioned relative to the target site.

6. The system of claim 1, wherein the one or more processors are further configured to determine the regional oxygen saturation ($rSO_2$) of the subject in response to determining that the regional oximetry sensor is positioned within or at the target site.

7. The system of claim 1, wherein the first metric value is based on a near-infrared light component of the first signal, and the second metric value is based on a near-infrared light component of the second signal, and
   wherein the one or more processors are configured to determine that the regional oximetry sensor is properly positioned relative to the target site by at least comparing the first combination metric value and the second combination metric value to a distribution threshold, wherein the distribution threshold is a function of the first metric value and the second metric value.

8. The system of claim 1, wherein the one or more processors are configured to determine the first metric value based on the first signal by at least normalizing the first signal based on a first calibration coefficient to generate a normalized first signal, and determining the first metric value based on the normalized first signal, and
   wherein the one or more processors are configured to determine the second metric value based on the second signal by at least normalizing the second signal based on a second calibration coefficient to generate a normalized second signal, and determining the second metric value based on the normalized second signal.

9. The system of claim 8, wherein the regional oximetry sensor comprises a light source configured to emit a plurality of wavelengths of light, wherein the first and second detectors of the regional oximetry sensor are configured to receive the plurality of wavelengths of light, and wherein:
   the first calibration coefficient is based on a brightness of the light source and a first sensitivity of the first detector, and
   the second calibration coefficient is based on the brightness of the light source and a second sensitivity of the second detector.

10. The system of claim 8, wherein the one or more processors are configured to determine at least one of the first metric value or the second metric value by at least determining the at least one of the first metric value or the second metric value as a logarithm of a respective one of the normalized first signal or the normalized second signal.

11. The system of claim 1, wherein the one or more processors are configured to determine the first combination metric value by at least determining First Metric−m*Second Metric+b, wherein m and b denote linear regression coefficients, wherein First Metric denotes the first metric value, and wherein Second Metric denotes the second metric value.

12. The system of claim 1, wherein the one or more processors are further configured to:
   determine a first morphology metric value associated with morphology of the first signal; and
   determine a second morphology metric value associated with morphology of the second signal, wherein the one or more processors are further configured to determine that the regional oximetry sensor is properly positioned relative to the target site based on the first and second morphology metric values.

13. The system of claim 12, wherein the first signal is associated with a first mean path length and the second signal is associated with a second mean path length longer than the first mean path length, and wherein the one or more processors are configured to determine the first morphology metric value based on a shape of a pulsatile modulation of the first signal.

14. The system of claim 12, wherein the first morphology metric value is based on skewness of a first derivative of the first signal, and wherein the second morphology metric value is based on the peak-to-peak modulation of the second signal.

15. A system comprising:
   one or more inputs configured to:
      receive a first signal representative of an intensity of light at a first detector of a regional oximetry sensor, and
      receive a second signal representative of an intensity of light at a second detector of the regional oximetry sensor; and
   one or more processors configured to:
      determine a first metric value based on the first signal;
      determine a second metric value based on the second signal, determine a combination metric value based on the first metric value and the second metric value;

determine, based on the combination metric value, that the regional oximetry sensor is not properly positioned relative to a target site on a subject.

16. The system of claim 15, wherein the one or more processors are configured to determine that the regional oximetry sensor is not properly positioned relative to the target site by at least comparing the combination metric value to a distribution threshold.

17. The system of claim 15, wherein the one or more processors are configured to use a neural network to determine, based on the combination metric value, that the regional oximetry sensor is not properly positioned relative to the target site.

18. A method comprising:

receiving a first signal representative of an intensity of light at a first detector of a regional oximetry sensor;

receiving a second signal representative of an intensity of light at a second detector of the regional oximetry sensor;

determining, by one or more processors, a first metric value based on the first signal;

determining, by the one or more processors, a second metric value based on the second signal;

determining, by the one or more processors, a first combination metric value based on the first metric value and the second metric value;

determining, by the one or more processors, a second combination metric value based on the first metric value and the second metric value; and determining, by one or more processors, based on the first combination metric value and the second combination metric value, that the regional oximetry sensor is properly positioned relative to a target site on a subject.

19. The method of claim 18, wherein the determining, by the one or more processors, that the regional oximetry sensor is properly positioned relative to the target site comprises comparing the first combination metric value to a first distribution threshold and comparing the second combination metric value to a second distribution threshold.

20. The method of claim 19, wherein the determining, by the one or more processors, that the regional oximetry sensor is properly positioned relative to the target site comprises determining that the first combination metric value exceeds the first distribution threshold and that the second combination metric does not exceed the second distribution threshold.

21. The method of claim 18, wherein the determining, by the one or more processors, that the regional oximetry sensor is properly positioned relative to the target site comprises using a neural network to determine that the regional oximetry sensor is properly positioned relative to the target site based on the first combination metric value and the second combination metric value.

22. A method comprising:

receiving a first signal representative of an intensity of light at a first detector of a regional oximetry sensor;

receiving a second signal representative of an intensity of light at a second detector of the regional oximetry sensor;

determining, by one or more processors, a first metric value based on the first signal;

determining, by the one or more processors, a second metric value based on the second signal;

determining, by the one or more processors, a combination metric value based on the first metric value and the second metric value; and determining, by one or more processors, based on the combination metric value, that the regional oximetry sensor is not properly positioned relative to a target site on a subject.

23. The method of claim 22, wherein the determining, by the one or more processors, that the regional oximetry sensor is not properly positioned relative to the target site comprises comparing the combination metric value to a distribution threshold.

24. The method of claim 22, wherein the determining, by the one or more processors, that the regional oximetry sensor is not properly positioned relative to the target site comprises using a neural network to determine that the regional oximetry sensor is properly positioned relative to the target based on the combination metric value.

* * * * *